(12) United States Patent
Sah

(10) Patent No.: US 8,697,127 B2
(45) Date of Patent: Apr. 15, 2014

(54) METHOD FOR PREPARING MICROSPHERES AND MICROSPHERES PRODUCED THEREBY

(75) Inventor: Hong Kee Sah, Seoul (KR)

(73) Assignees: Ewha University-Industry Collaboration Foundation, Seoul (KR); SK Chemicals Co., Ltd., Suwon (KR)

( * ) Notice: Subject to any disclaimer, the term of this patent is extended or adjusted under 35 U.S.C. 154(b) by 0 days.

(21) Appl. No.: 13/106,400

(22) Filed: May 12, 2011

(65) Prior Publication Data

US 2011/0217341 A1    Sep. 8, 2011

Related U.S. Application Data

(63) Continuation of application No. PCT/KR2009/006690, filed on Nov. 13, 2009.

(30) Foreign Application Priority Data

Nov. 14, 2008    (KR) .......................... 10-2008-113304

(51) Int. Cl.
*A61K 9/14* (2006.01)
(52) U.S. Cl.
USPC ............ 424/484; 424/400; 424/486; 424/489
(58) Field of Classification Search
None
See application file for complete search history.

(56) References Cited

U.S. PATENT DOCUMENTS

2004/0126431 A1    7/2004  Lagarce et al.
2008/0220070 A1    9/2008  Fu et al.

OTHER PUBLICATIONS

Kim, J., et al., Ammonolysis-Induced Solvent Removal: A Facile Approach for Solidifying Emulsion Droplets into PLGA Microspheres, Biomacromolecules, 2007, 8, 3900-3907.*
Bernhard et al., Specific Effects in Acid Catalysis by Ion Exchange Resins. I. Hydrolysis of Esters in 70% Aqueous Acetone, J. Am. Chem. Soc., 1953, 75 (8) 1798-1800.*
Khurana et al., Facile Hydrolysis of Esters with KOH-Methanol at Ambient Temperature, Monatshefte fur Chemie, 2004 (135) 83-87.*
Kim, J., et al., Ammonolysis-Induced Solvent Removal: A Facile Approach for Solidifying Emulsion Droplets into PLGA Microspheres, Biomacromolecules, 2007, 8, 3900-3907 (Kim).*
Bernhard et al., Specific Effects in Acid Catalysis by Ion Exchange Resins. I. Hydrolysis of Esters in 70% Aqueous Acetone, J. Am. Chem. Soc., 1953, 75 (8) 1798-1800 (Bernhard).*
Khurana et al., Facile Hydrolysis of Esters with KOH-Methanol at Ambient Temperature, Monatshefte fur Chemie, 2004 (135) 83-87 (Khurana).*
Kang, F. et al., "Effect of Additives on the Release of a Model Protein from PLGA Microspheres", AAPS PharmSciTech, 2 (4) article 30 (2001).
O'Donnell, P. et al., "Preparation of microspheres by the solvent evaporation technique", Advanced Drug Delivery Reviews, vol. 28, pp. 25-42 (1997).

* cited by examiner

*Primary Examiner* — Kevin S Orwig
*Assistant Examiner* — Dominic Lazaro
(74) *Attorney, Agent, or Firm* — Edwards Wildman Palmer LLP

(57)    ABSTRACT

The present invention relates to a method for preparing microspheres and microspheres prepared thereby, more particularly to a method for preparing a polymeric microsphere, including preparing an emulsion including a polymer compound, a drug, a water-insoluble organic solvent and a dispersion solvent and adding to the prepared emulsion a base or an acid to remove the water-insoluble organic solvent from the emulsion, a polymeric microsphere prepared thereby, and a composition for drug delivery including the microsphere. According to the present invention, a drug-containing polymer microsphere may be prepared quickly and simply without the solvent evaporation or solvent extraction process, thereby reducing water consumption and minimizing wastewater generation.

7 Claims, 29 Drawing Sheets

METHOD FOR PREPARING MICROSPHERES AND MICROSPHERES PRODUCED THEREBY

CROSS-REFERENCES TO RELATED APPLICATION

This is a continuation of International Application No. PCT/KR2009/006690, with an international filing date of Nov. 13, 2009, which claims the benefit of Korean Application No. 10-2008-113304 filed Nov. 14, 2008, the entire contents of which are incorporated herein by reference.

TECHNICAL FIELD

The present invention relates to a method for preparing microspheres and microspheres prepared thereby, more particularly to a method for preparing a polymeric microsphere, including preparing an emulsion including a polymer compound, a drug, a water-insoluble organic solvent and a dispersion solvent and adding to the prepared emulsion a base or an acid to remove the water-insoluble organic solvent from the emulsion, a polymeric microsphere prepared thereby, and a composition for drug delivery including the microsphere.

BACKGROUND ART

Conventional injectable formulations such as solution, suspension, and emulsion are quickly removed from the body after administration, and therefore frequent administration is essentially needed for treatment of chronic diseases. Microencapsulation has been developed to solve the problem, and referred to a production process for encapsulating drugs in microspheres (hereinafter, the term microsphere will include nanospheres) consisting of high molecular compounds. Microspheres are usually in a size of μm unit, and can be administered to a human or animal by intramuscular or subcutaneous injection. Further, microspheres can be produced to have a variety of drug release rates, so that the period of drug delivery can be controlled. Therefore, even if a therapeutic drug is administered only once, its effective concentration can be maintained over a long period of time, and the total administration amount of therapeutic drug can be minimized to improve the drug compliance in patients. Accordingly, world famous pharmaceutical companies are very interested in the production of polymeric microsphere loaded with drugs.

In the production of polymeric microspheres by microencapsulation, poly-d,l-lactide-co-glycolide (PLGA) has been most widely used as a high molecular compound. PLGA is a biocompatible high molecular compound that is hydrolyzed in vivo to be converted into nontoxic lactic acid and glycolic acid. Therefore, pharmaceutical industries have made extensive studies on the development of drug formulation using PLGA, and examples of current available microsphere product produced by using PLGA include Risperdal Consta, Sandostatin LAR, Vivitrol, and Lupron Depot. Each of them is administered to a patient once to control the release of risperidone, octreotide acetate, naltrexone, and leuprolide acetate from 2 weeks to 4 months.

Such polymeric microspheres loaded with drugs can be conventionally produced by a solvent evaporation method or a solvent extraction method using an organic solvent such as methylene chloride and ethyl acetate.

First, the solvent evaporation method will be briefly described (see U.S. Pat. Nos. 6,471,996, 5,985,309, and 5,271,945). A drug is dispersed or dissolved in an organic solvent in which a high molecular compound is dissolved, and then emulsified in a dispersion medium such as water to produce an oil-in-water (O/W) emulsion. Then the organic solvent in the emulsion is diffused into a dispersion medium and evaporated across the air/water interface to form the polymeric microspheres loaded with drugs. At this time, in order to accelerate the diffusion of organic solvent into the dispersion medium, a method such as organic solvent extraction using reduced pressure, increased temperature, and an excessive amount of water is used. A dispersion organic solvent that is generally used to dissolve the high molecular PLGA is methylene chloride, which dissolves a PLGA copolymer well using various molecular weights and lactide: glycolide ratios and because it does not mix well with water due to the low water solubility of 1.32% by weight. Thus, methylene chloride is a suitable solvent for the production of oil-in-water emulsion. Further, due to the low boiling point of 39.8° C., a small amount of methylene chloride molecules that diffused from emulsion liquid droplets into water are evaporated across the water/air interface. Such process is continuously repeated to remove methylene chloride from emulsion droplets, thereby forming microspheres. Finally, the residual methylene chloride present in microspheres is easily dried and removed due to its low boiling point.

Likewise, even though methylene chloride is the most optimal solvent used for the production of emulsion in that it is very volatile, not mixed well with water, and has a lower boiling point than water, methylene chloride has the following problems: (a) it is a carcinogen proved by experiments; (b) it destroys the ozone layer in the atmosphere to generate a toxic environment, causing an increase in human skin cancer; (c) it is one of the 38 toxic and hazardous substances announced by the agency for toxic substances and disease registry within the US Department of Health and Human Services; (d) a lot of time is required to completely remove methylene chloride in the emulsion droplets, since it has a low water solubility of about 1.32% by weight and only a small amount of methylene chloride is dissolved in water and evaporates. For example, in U.S. Pat. No. 6,884,435, the emulsion is stirred overnight to remove methylene chloride from the emulsion, and conditions such as increased temperature or reduced pressure in a reactor are introduced to shorten the production time of microspheres (see U.S. Pat. Nos. 3,691,090, 3,891,570, 6,270,700, and 6,572,894).

On the other hand, the solvent extraction method used to produce polymeric microspheres loaded with drugs is a method for effectively extracting the organic solvent in the emulsion droplets by using a large amount of solubilizing solvent. When the organic solvent is extracted from the emulsion droplets, the dissolved high molecular compounds are hardened to convert the emulsion droplets into microspheres. The solubilizing solvent that is generally used is water, and the degree of water solubility of the organic solvent greatly affects the amount of water needed. For example, methylene chloride has water solubility of 1.32% by weight, whereby a very large amount of water is needed for extracting methylene chloride in the emulsion. However, a large amount of wastewater containing methylene chloride is produced, in which the treatment of the wastewater becomes a problematic issue. Therefore, in the solvent extraction method, ethyl acetate, which has higher water solubility than methylene chloride, is mainly used. Since ethyl acetate has the water solubility of 8.7% by weight, it can be extracted by using a relatively small amount of water, as compared to methylene chloride, and it is advantageously a nonhalogenated organic solvent. However, its boiling point is 77° C. and much higher than 39.8° C., which is that of methylene chloride. Thus, ethyl acetate has a drawback that the residual solvent is hard to remove when dried. Furthermore, a high molecular PLGA compound with a specific molecular weight and lactide:glycolide ratio has a characteristic of not dissolving easily in ethyl acetate.

Therefore, technologies simultaneously employing the solvent evaporation method and solvent extraction method are disclosed in U.S. Pat. Nos. 4,389,840, 4,530,840, 6,544,559, 6,368,632, and 6,572,894. That is, in the methods, the emulsion is produced, and then the organic solvent is partially removed by the evaporation process, and the residual organic solvent is removed by the solvent extraction method. For example, U.S. Pat. No. 4,389,840 discloses a method for producing microspheres, in which a drug and a high molecular PLGA are dissolved in methylene chloride and then emulsified in water to produce oil in water-type emulsion, then 40 to 60% by weight of methylene chloride is removed by the evaporation process, and the residual methylene chloride is extracted using a large amount of water to produce microspheres.

However, since all of the organic solvents used in the known methods do not have sufficient high water solubility, excessively large amounts of water (over 10 times more than water solubility of organic solvent) should be used. Thus, a large-volume reactor is needed, and a large amount of wastewater containing organic solvent is produced, as a result, the cost for wastewater treatment is increased. Further, there is a problem that the residual organic solvent present in the microspheres is not effectively removed.

In particular, when a large amount of organic solvent remains in the microspheres, the microspheres tend to coalesce during the drying process. As a result, since the microspheres may not be dispersed separately after the drying process, a problem may occur during injection and the reproducibility of drug release may decrease. Further, if the amount of the remaining solvent exceeds an allowable limit, it will be difficult to get the regulatory approval.

SUMMARY OF DISCLOSURE

The inventors of the present invention have researched to develop a method capable of solving the aforesaid problem and preparing a polymer microsphere including a drug in a simple and easy way. As a result, we have found that a polymer microsphere can be simply prepared by preparing an emulsion including a water-insoluble organic solvent and a dispersion solvent, and chemically decomposing the organic solvent using a base or an acid to converting it into a water-soluble solvent, so that the organic solvent remaining in the emulsion droplet is continuously diffused toward the aqueous phase, thereby effectively inducing the decomposition and hardening the emulsion droplet into a microsphere.

Accordingly, an object of the present invention is to provide a novel method for preparing a polymer microsphere by adding a base or an acid to an emulsion including a polymer, a drug, a water-insoluble organic solvent and a dispersion solvent to remove the water-insoluble organic solvent.

To achieve the object, the present invention provides a method for preparing a polymeric microsphere, including:

(a) preparing an oil-in-water (O/W), oil-in-oil (O/O) or water-in-oil-in-water (W/O/W) emulsion including a polymer compound, a drug, a water-insoluble organic solvent and a dispersion solvent and (b) adding to the emulsion prepared in (a) a base solution or an acid solution to remove the water-insoluble organic solvent from the emulsion.

The present invention further provides a polymeric microsphere prepared by the preparation method of the present invention.

To achieve the object, the present invention further provides a composition for drug delivery comprising the polymer microsphere as an effective ingredient.

DETAILED DESCRIPTION

Figure 1:
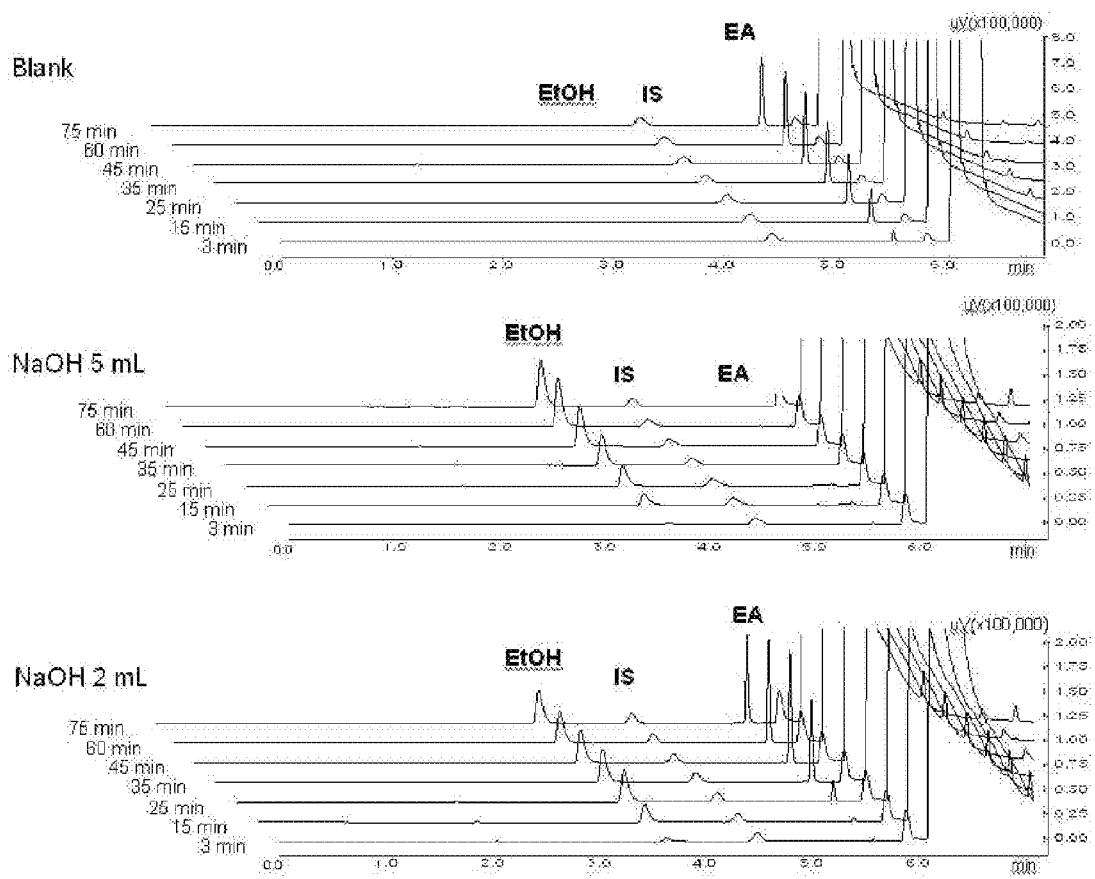
FIG. 1 shows gas chromatography (GC) chromatograms of an aqueous phase sample depending on time of an ethyl acetate/aqueous phase system following slow stirring.

Hereinafter, the present invention will be described in more detail. The method for preparing a polymeric microsphere of the present invention may include (a) preparing an oil-in-water (O/W), oil-in-oil (O/O) or water-in-oil-in-water (W/O/W) emulsion including a polymer compound, a drug, a water-insoluble organic solvent and a dispersion solvent; and (b) adding to the emulsion prepared in (a) a base solution or an acid solution to remove the water-insoluble organic solvent from the emulsion.

Each step of the method for producing polymeric microspheres according to the present invention will be described in detail as follows.

(a): Preparation of Emulsion

An oil-in-water (O/W), oil-in-oil (O/O) or water-in-oil-in-water (W/O/W) emulsion comprising a polymer compound, a drug, a water-insoluble organic solvent and a dispersion solvent is prepared.

The emulsion may be prepared by a method commonly used in the art. More specifically, in order to prepare an oil-in-water (O/W) type or oil-in-oil (O/O) type emulsion, a dispersed phase comprising a polymer compound, a drug and a water-insoluble organic solvent is added to a dispersion solvent. And, in order to prepare a water-in-oil-in-water (W/O/W) emulsion, an aqueous solution in which a drug is dissolved, is emulsified in a water-insoluble organic solvent in which a polymer compound is dissolved, so as to form a W/O (water-in-oil) type emulsion, and then added to the dispersion solvent to produce a W/O/W (water-in-oil-in-water) type emulsion.

The polymer compound for preparing the polymeric microsphere may be used without limitation if it is well known in the art, however, preferably, it may be polylactic acid, polylactide, polylactic-co-glycolic acid, polylactide-co-glycolide (PLGA), polyphosphazine, polyiminocarbonate, polyphosphoester, polyanhydride, polyorthoester, a copolymer of lactic acid and caprolactone, polycaprolactone, polyhydroxyvalerate, polyhydroxybutyrate, polyamino acid, a copolymer of lactic acid and amino acid, and a mixture thereof.

The drug used in the present invention may include all of hydrophilic drugs and hydrophobic drugs and it may be used without limitation if it is able to be encapsulated to polymeric microspheres. Examples of the drug include progesterone, haloperidol, thiothixene, olanzapine, clozapine, bromperidol, pimozide, risperidone, ziprasidone, diazepam, ethyl loflazepate, alprazolam, nemonapride, fluoxetine, sertraline, venlafaxine, donepezil, tacrine, galantamine, rivastigmine, selegiline, ropinirole, pergolide, trihexyphenidyl, bromocriptine, benztropine, colchicine, nordazepam, etizolam, bromazepam, clotiazepam, mexazolum, buspirone, goserelin acetate, somatotropin, leuprolide acetate, octreotide, cetrorelix, sandostatin acetate, gonadotropin, fluconazole, itraconazole, mizoribine, cyclosporin, tacrolimus, naloxone, naltrexone, cladribine, chlorambucil, tretinoin, carmustine, anagrelide, doxorubicin, anastrozole, idarubicin, cisplatin, dactinomycin, docetaxel, paclitaxel, raltitrexed, epirubicin, letrozole, mefloquine, primaquine, oxybutynin, tolterodine, allylestrenol, lovostatin, simvastatin, pravastatin, atorvastatin, alendronate, salcatonin, raloxifene, oxandrolone, conjugated estrogen, estradiol, estradiol valerate, estradiol benzoate, ethinyl estradiol, etonogestrel, levonorgestrel, tibolone, norethisterone and piroxicam and it also may be macro molecules such as proteins or nucleic acid.

The water-insoluble organic solvent used in the present invention may be used without limitation if it is well known in the art, as long as it is capable of dissolving the polymer which is used for the preparation of the polymeric microspheres, being hydrolyzed by an acid or a base, and being hydrolyzed into water-soluble products. In general, compounds having backbone of amide, ester, anhydride and halogen acid are known to be easily hydrolyzed by an acid or a base.

Compounds having backbone of anhydride are hydrolyzed to produce water-soluble carboxylic acids, and compounds having backbone of ester are hydrolyzed into carboxylic acid and alcohol. Compounds having backbone of acid halogen are hydrolyzed into carboxylic acid and halogen acid (HF, HCl, Hbr, HI etc). Since compounds having backbone of amide are hydrolyzed into carboxylic acid and amine, if the produced amine is water-soluble, the corresponding amide may be included in the water-insoluble organic solvent of the present invention.

The water-insoluble organic solvent of the present invention may be compounds having backbone of acid halogen, compounds having backbone of anhydride, compounds having backbone of phosphoric anhydride, compounds having backbone of ester, compounds having backbone of carboxylic esters, compounds having backbone of phosphoric esters, compounds having backbone of sulfuric acid esters, compounds having backbone of nitric esters, compounds having backbone of boric acid, compounds having backbone of amide and compounds having backbone of carboxylic amides, preferably, methyl acetate, ethyl acetate, propyl acetate, isopropyl acetate, butyl acetate, methyl formate, ethyl formate, isopropyl formate, propyl formate, butyl formate, methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, maleic anhydride, acetic anhydride, propionic anhydride, phosphoric anhydride, acetamide, propionamide, butylamide and carboxylamide.

More specifically, it is preferable that the water-insoluble organic solvent is selected from the group consisting of ethyl acetate, methyl acetate, methyl formate, ethyl formate, isopropyl formate, propyl formate, acetic anhydride or propionic anhydride.

Further, if necessary, the water-insoluble organic solvent may control solubility of the drug to be encapsulated in the microsphere or control the hardening speed of the emulsion droplet, as desired, by using a co-solvent prepared by mixing one or more different organic solvents.

The dispersion solvent used in the present invention includes an aqueous dispersion solvent containing an emulsifier or non-aqueous dispersion solvent, and the aqueous dispersion solvent is used for the preparation of an O/W type and W/O/W type emulsion, the non-aqueous dispersion solvent is used for the preparation of an O/O type emulsion. As the aqueous dispersion solvent, an aqueous solution containing hydrophilic emulsifier such as polyvinyl alcohol or polysorbates (for example, polysorbate 20, polysorbate 60, polysorbate 65, polysobate 80, polysorbate 85) or a co-solvent thereof can be used. As the non-aqueous dispersion solvent, silicone oil, vegetable oil, toluene, or xylene containing lipophilic emulsifier such as glycerin esters of fatty acids or lecithin can be used. The concentration of the emulsifier in the dispersion solvent may be 0.05 to 15% (w/v).

The polymer may be included in an amount of 1 to 500 parts by weight, preferably 1 to 50 parts by weight, based on 1 part by weight of the drug. The concentration of the polymer in the emulsion may be 3 to 30% (w/v).

The volume ratio of the dispersed phase or the W/O (water-in-oil) type emulsion to the dispersion solvent may be 1:1-100, preferably 1:3-15. And, the volume ratio of the aqueous solution in which the drug is dissolved, to the water-insoluble organic solvent in which the polymer is dissolved, may be 1:1-50, preferably 1:2-20.

(b): Removal of Water-Insoluble Organic Solvent from Emulsion

A base or an acid solution is added to the O/W, W/O/W or O/O emulsion prepared in (a) to remove the water-insoluble organic solvent from the emulsion.

In the present invention, the removal of the water-insoluble organic solvent from the emulsion by adding a base or acid solution is preferably accomplished by hydrolysis. Hydrolysis refers to a reaction which is decomposed into two products by adding water. Compounds having backbone of ester are hydrolyzed into carboxylic acid and alcohol, compounds having backbone of anhydride are hydrolyzed into carboxylic acids, compounds having backbone of amide are hydrolyzed into carboxylic acid and amine and compounds having backbone of acid halogen are hydrolyzed into carboxylic acid and halogen acid (such as HF, HCl, HBr, HI). Through this reaction, the water-insoluble organic solvent diffused (or dissolved) in small quantity in a layer (e.g., an aqueous layer (water phase)) is converted into a water-soluble organic solvent which is completely dissolved in water, and the water-insoluble organic solvent is diffused into the aqueous layer by that amount. As this process continues, the water-insoluble organic solvent is removed from the emulsion, thereby resulting in hardening of the emulsion droplet into a microsphere. As a result, a desired polymer microsphere including the drug can be prepared. The removal of the water-insoluble organic solvent from the emulsion includes, in addition to complete or substantial (to an extent not to be detected) removal of the water-insoluble organic solvent, reduction of the amount of the water-insoluble organic solvent as compared to before the addition of the acid or base. As the emulsion droplet is quickly hardened, the interaction between the emulsion droplet particles may be reduced and the desired microsphere may be obtained without coalescence. The acid catalyzes the reaction and the base is consumed during the reaction. If amount of the acid or base be added in less molar or more molar than that of the water-insoluble organic solvent, the reaction can always occur. However, since addition of too much acid or base may induce problem with respect to the stability of the drug and the polymer, a suitable amount thereof have to be considered. Preferably, the base solution may be added in such an amount that the molar ratio of the water-insoluble organic solvent to the base solution is 1:0.1-10, more preferably 1:0.1-5, further more preferably 1:0.2-3, the most preferably 1:0.2-1.5.

Preferably, the base may be NaOH, LiOH, KOH, $NH_4OH$, $Cu(OH)_2$ and $Fe(OH)_3$, and the acid may be HCl, $HNO_3$, $H_2SO_4$, $CH_3COOH$, $H_3BO_3$ and $H_2CO_3$. In the description, the base or acid is also referred to as a decomposition reagent. The polymeric microsphere prepared by the method of the present invention has an average particle size of 0.1 to 3500 μm, preferably 10 to 350 μm, and may comprise a variety amount of drug, as required.

According to the method of the present invention, a drug-containing polymeric microsphere may be prepared quickly and simply without the solvent evaporation or solvent extraction process, thereby reducing water consumption and minimizing wastewater generation.

The polymer microsphere of the present invention is capable of effectively delivering the drug included in the polymer microsphere. Therefore, the present invention provides a composition for drug delivery comprising the polymer microsphere prepared by the preparation method of the present invention as an effective ingredient.

As will be easily understood by those skilled in the art, the composition for drug delivery of the present invention may be applied to various diseases depending on the drug included therein.

The nucleotide or protein processing may be referred to the following literature [Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)].

In an example, GC analysis was carried out in order to investigate whether ethyl acetate, ethyl formate, propyl formate, and isopropyl formate are decomposed by an acid or base in an aqueous phase. When no reagent was added to the aqueous phase (blank), some of ethyl acetate, ethyl formate, propyl formate or isopropyl formate was transported into the aqueous phase, thereby increasing their concentration in the aqueous phase until saturation. When their concentration is saturated, their transportation into the aqueous phase does not occur. In contrast, when the acid or base was added, hydrolysis continued to occur, thereby increasing the concentration of the hydrolyzed product such as ethanol continuously.

In another example, it was investigated whether propionic anhydride is hydrolyzed by an acid or a base and is dissolved in the aqueous phase. When no acid or base was added, propionic anhydride mixed with 0.5% polyvinyl alcohol maintained an emulsion state. In contrast, when an acid or a base was added, the emulsion disappeared and a clear and transparent single phase appeared.

In another example, it was demonstrated that, when isopropyl formate is used and a base is used as a decomposition reagent, emulsion droplets can be quickly hardened to form microspheres by adding various amounts of the decomposition reagent to the aqueous phase. In contrast, when no decomposition reagent is added to the aqueous phase, the emulsion droplets were not hardened to form microspheres. Therefore, it can be seen that using of the decomposition reagent is important for the preparation of microspheres.

In another example, progesterone, anastrazole, olanzapine, risperidone, aripiprazole, docetaxel, piroxicam, rivastigmine or tolterodine was selected as target drugs, and microparticles in which the target drugs are encapsulated were prepared at various conditions. And it was observed that their properties, encapsulation ratio, residual amount of organic solvent, or the like. As a result, spherical microparticles encapsulating the target drug were prepared well, and they had high encapsulation ratio. Besides, the residual amount of organic solvent was very low level.

The present invention provides a novel method for preparing a polymeric microsphere comprising the step of removing a water-insoluble organic solvent using a base or an acid, a polymeric microsphere prepared by the method, and a composition for drug delivery comprising the polymeric microsphere. According to the present invention, a drug-containing polymer microsphere may be prepared quickly and simply without the solvent evaporation or solvent extraction process, thereby reducing water consumption and minimizing wastewater generation.

FIG. 1 shows gas chromatography (GC) chromatograms of an aqueous phase sample depending on time of an ethyl acetate/aqueous phase system following slow stirring. Each chromatogram is for the case where no decomposition reagent was added to the aqueous phase, and 2 mL or 5 mL of 10 M NaOH was added (EA=ethyl acetate, IS=internal standard, EtOH=ethanol).

Figure 2:
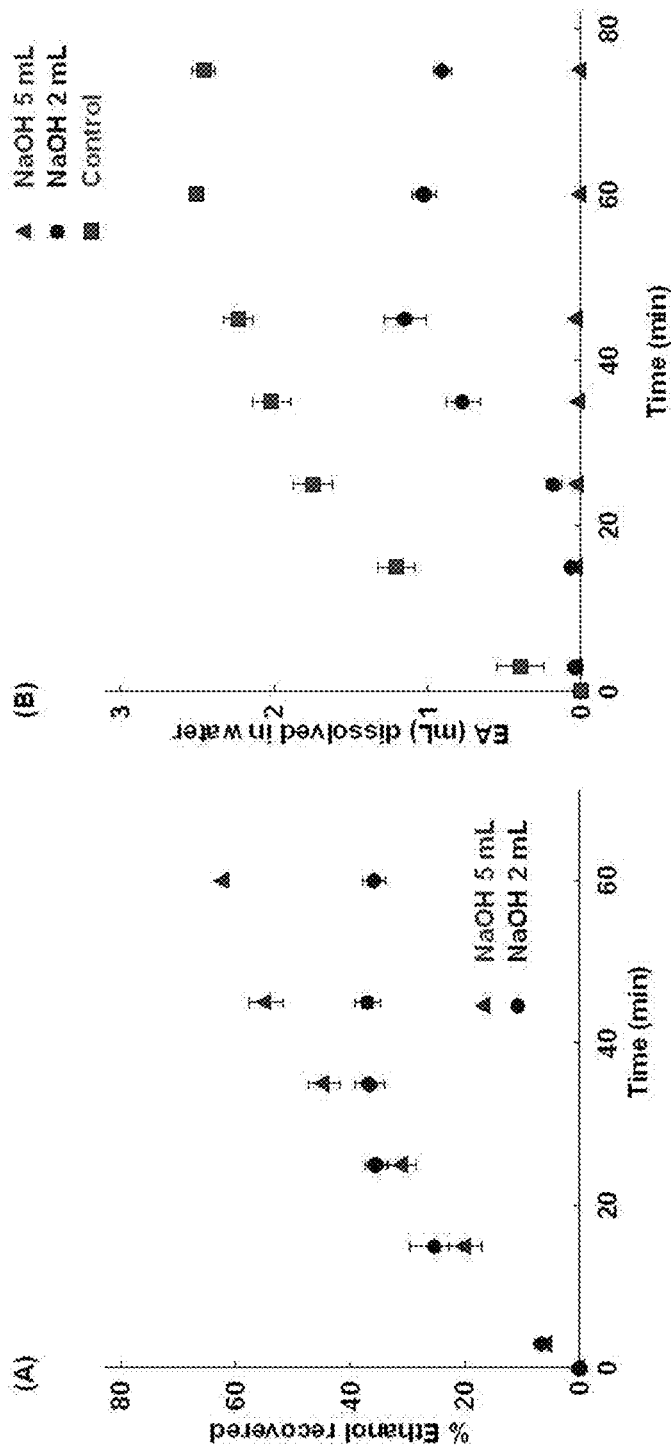
FIG. 2 shows a change of ethanol and ethyl acetate concentrations in the aqueous phase depending on time.

FIG. 2 shows a change of ethanol and ethyl acetate concentrations in the aqueous phase depending on time. (A) Ethanol concentration in the aqueous phase when 2 mL or 5 mL of M NaOH was added. (B) Ethyl acetate concentration in the aqueous phase when no NaOH was added, and 2 mL or 5 mL of 10 M NaOH was added.

Figure 3:
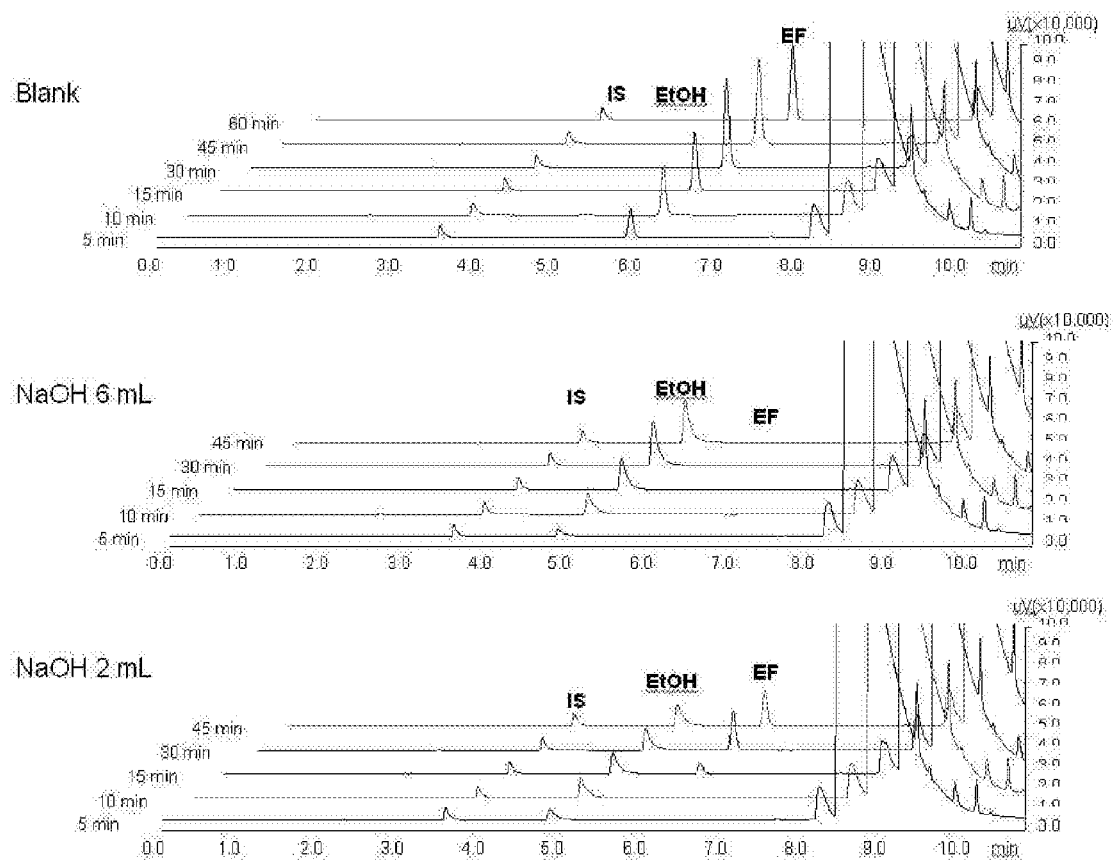
FIG. 3 shows GC chromatograms of an aqueous phase sample depending on time of an ethyl formate/aqueous phase system following slow stirring.

FIG. 3 shows GC chromatograms of an aqueous phase sample depending on time of an ethyl formate/aqueous phase system following slow stirring. Each chromatogram is for the case where no decomposition reagent was added to the aqueous phase, and 2 mL or 5 mL of 10 M NaOH was added (EF=ethyl formate, IS=internal standard, EtOH=ethanol).

Figure 4:
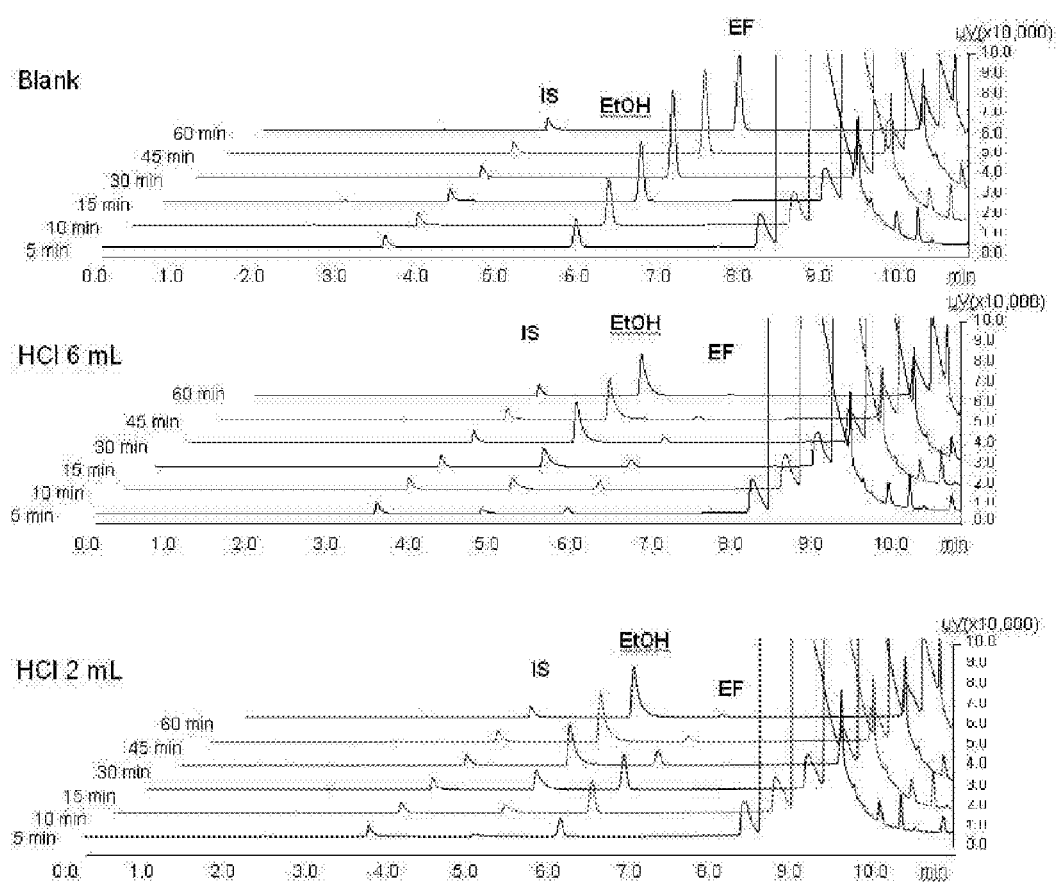
FIG. 4 shows GC chromatograms of an aqueous phase sample depending on time of an ethyl formate/aqueous phase system following slow stirring.

FIG. 4 shows GC chromatograms of an aqueous phase sample depending on time of an ethyl formate/aqueous phase system following slow stirring. Each chromatogram is for the case where no decomposition reagent was added to the aqueous phase, and 2 mL or 6 mL of 10 M HCl was added (EF=ethyl formate, IS=internal standard, EtOH=ethanol).

Figure 5:
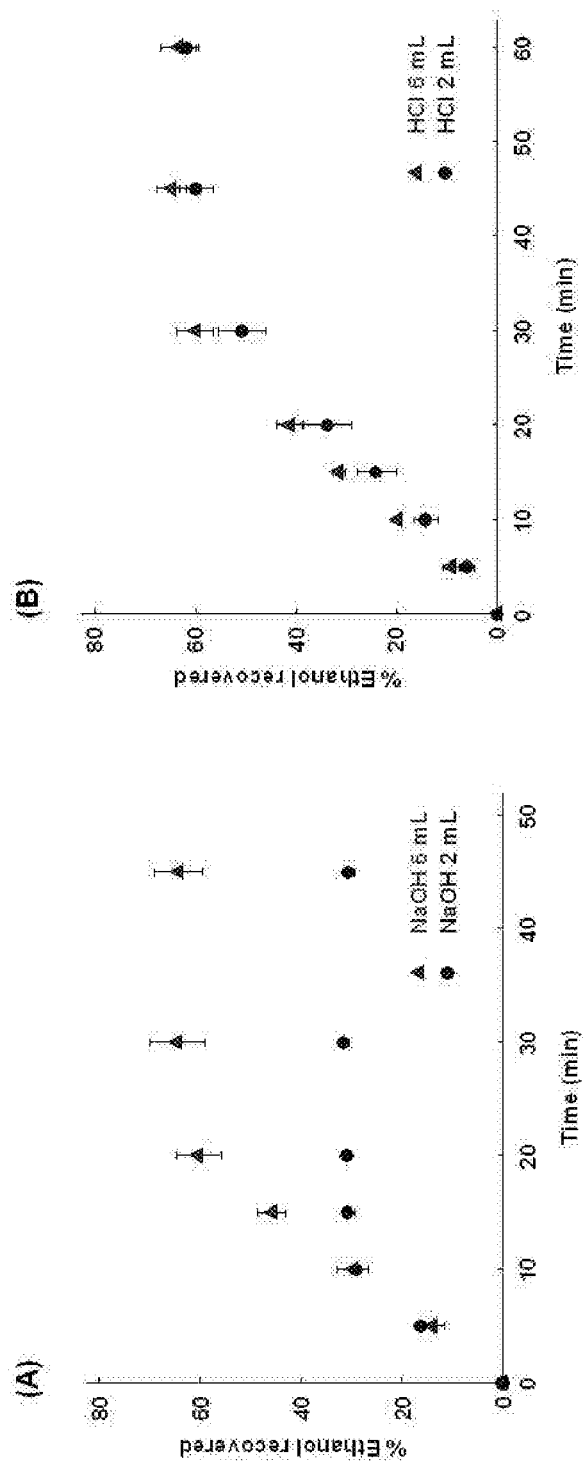
FIG. 5 shows a change of ethanol concentration in the aqueous phase depending on time.

FIG. 5 shows a change of ethanol concentration in the aqueous phase depending on time. (A) Ethanol concentration in the aqueous phase when 2 mL or 5 mL of 10 M NaOH was added. (B) Ethanol concentration in the aqueous phase when 2 mL or 6 mL of 10 M HCl was added.

Figure 6:
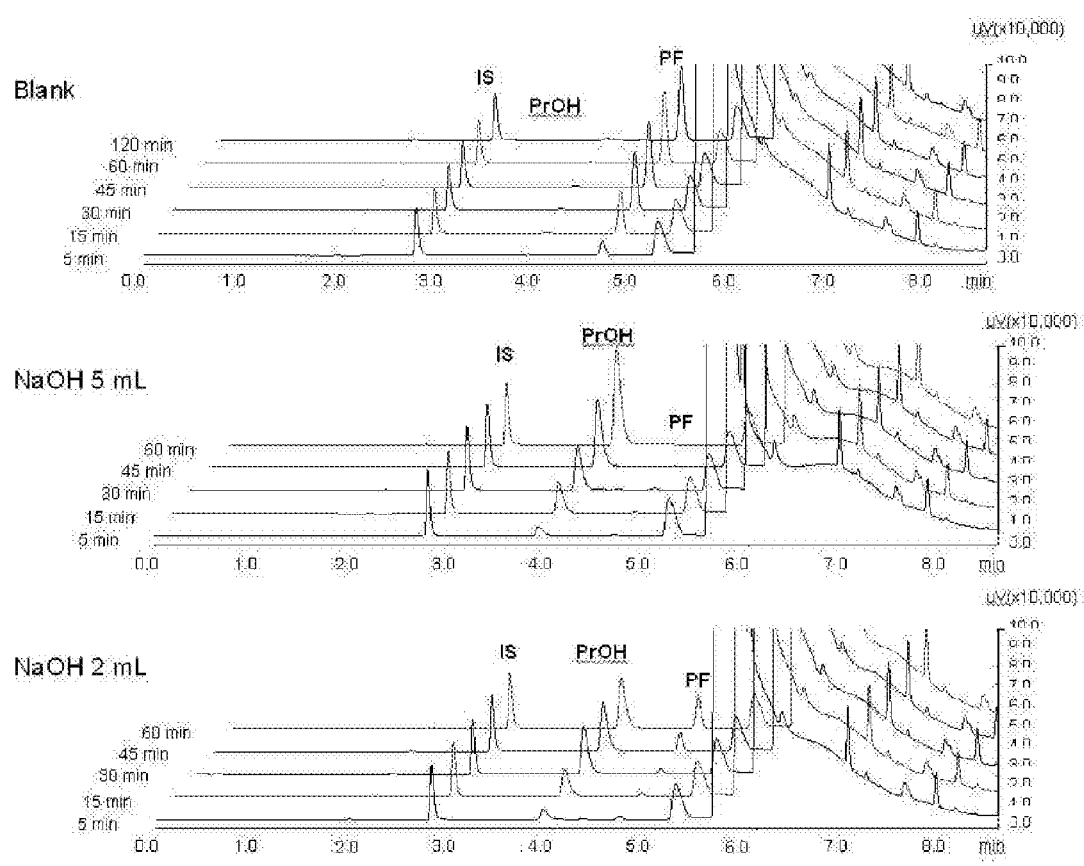
FIG. 6 shows GC chromatograms of an aqueous phase sample depending on time of a propyl formate/aqueous phase system following slow stirring.

FIG. 6 shows GC chromatograms of an aqueous phase sample depending on time of a propyl formate/aqueous phase system following slow stirring. Each chromatogram is for the case where no decomposition reagent was added to the aqueous phase, and 2 mL or 5 mL of 10 M NaOH was added (PF=propyl formate, IS=internal standard, PrOH=propanol).

Figure 7:
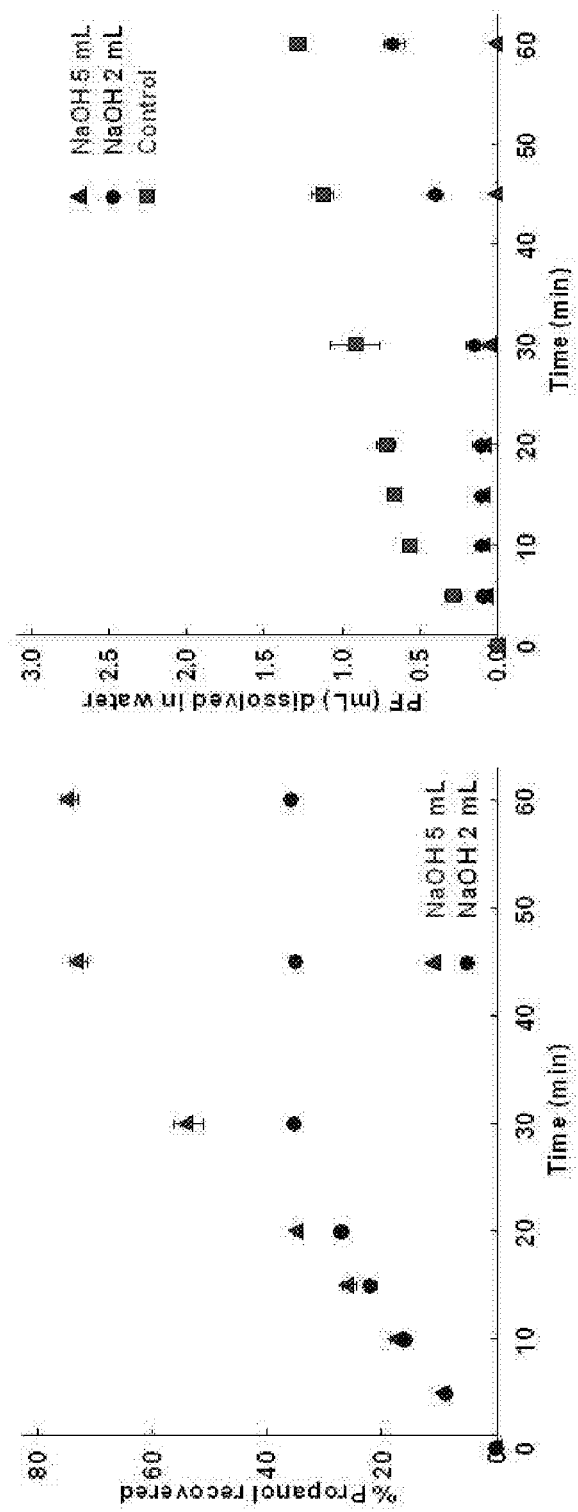
FIG. 7 shows a change of propanol/propyl formate concentrations in the aqueous phase depending on time.

FIG. 7 shows a change of propanol/propyl formate concentrations in the aqueous phase depending on time. (A) Propanol concentration in the aqueous phase when 2 mL or 5 mL of 10 M NaOH was added. (B) Propyl formate concentration in the aqueous phase when no decomposition reagent was added to the aqueous phase, and 2 mL or 5 mL of 10 M NaOH was added.

Figure 8:
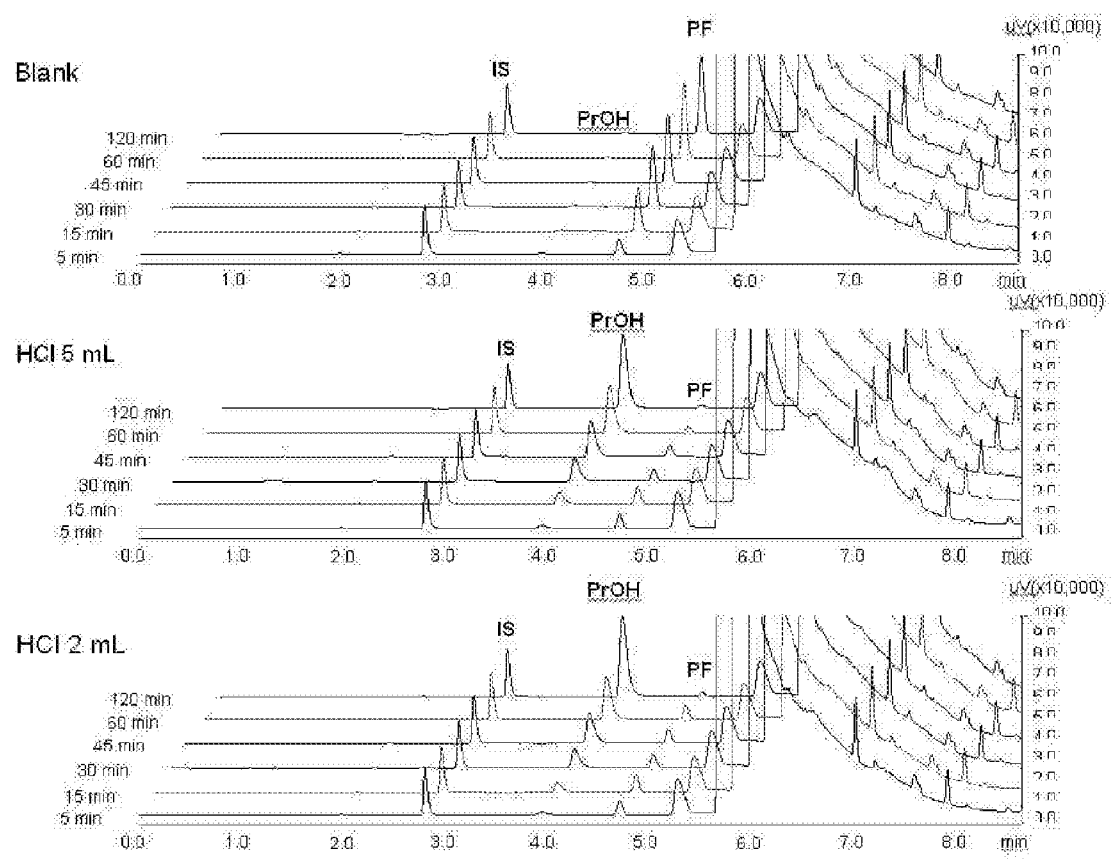
FIG. 8 shows GC chromatograms of an aqueous phase sample depending on time of a propyl formate/aqueous phase system following slow stirring.

FIG. 8 shows GC chromatograms of an aqueous phase sample depending on time of a propyl formate/aqueous phase system following slow stirring. Each chromatogram is for the case where no decomposition reagent was added to the aqueous phase, and 2 mL or 5 mL of 10 M HCl was added (PF=propyl formate, IS=internal standard, PrOH=propanol).

Figure 9:
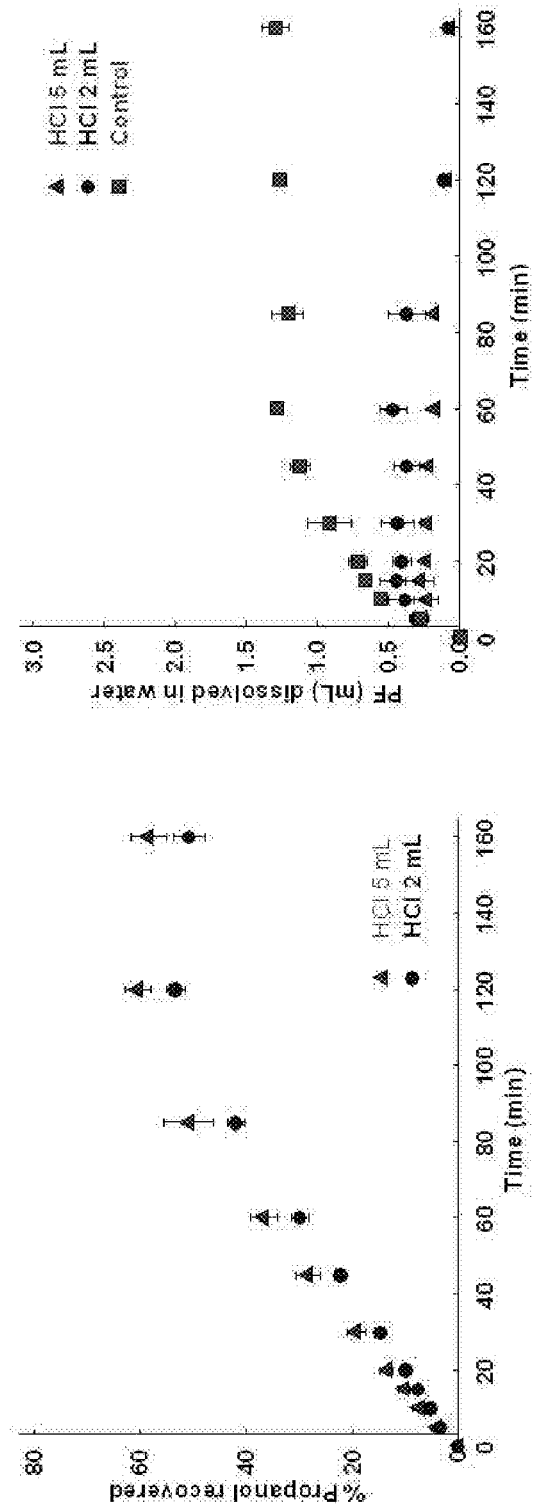
FIG. 9 shows a change of propanol/propyl formate concentrations in the aqueous phase depending on time.

FIG. 9 shows a change of propanol/propyl formate concentrations in the aqueous phase depending on time. (A) Propanol concentration in the aqueous phase when 2 mL or 5 mL of 10 M HCl was added. (B) Propyl formate concentration in the aqueous phase when no decomposition reagent was added to the aqueous phase, and 2 mL or 5 mL of 10 M HCl was added.

Figure 10:
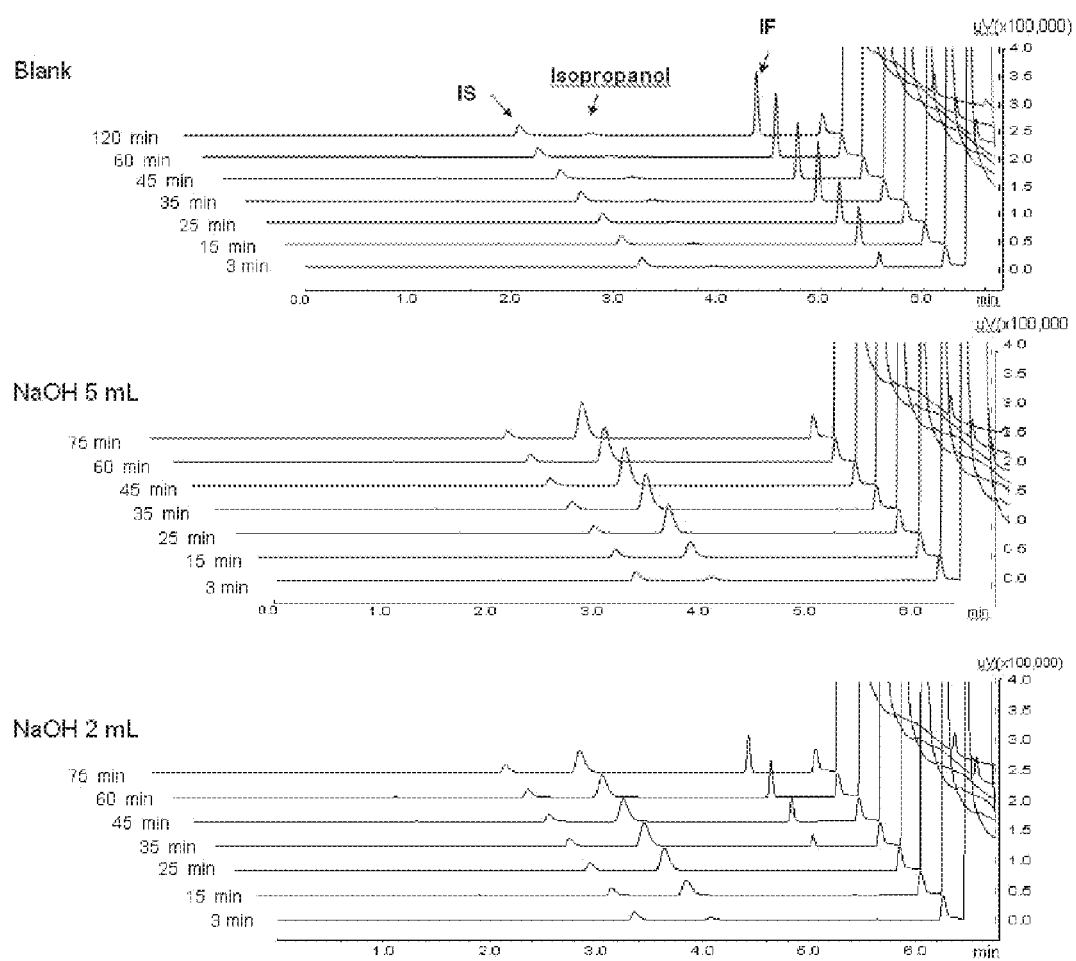
FIG. 10 shows GC chromatograms of an aqueous phase sample depending on time of an isopropyl formate/aqueous phase system following slow stirring.

FIG. 10 shows GC chromatograms of an aqueous phase sample depending on time of an isopropyl formate/aqueous phase system following slow stirring. Each chromatogram is for the case where no decomposition reagent was added to the aqueous phase, and 2 mL or 5 mL of 10 M NaOH was added (IF=isopropyl formate, IS=internal standard).

Figure 11:
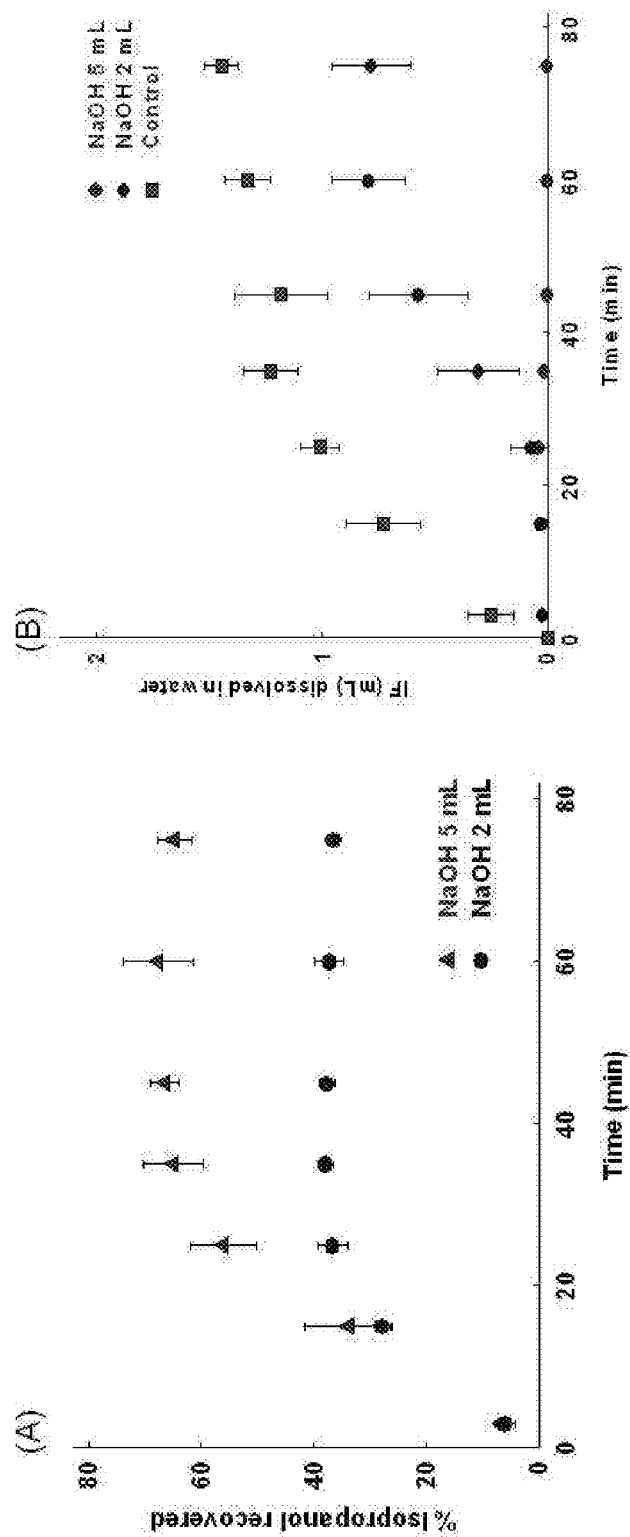
FIG. 11 shows a change of isopropanol/isopropyl formate concentrations in the aqueous phase depending on time.

FIG. 11 shows a change of isopropanol/isopropyl formate concentrations in the aqueous phase depending on time. (A) Isopropanol concentration in the aqueous phase when 2 mL or 5 mL of 10 M NaOH was added. (B) Isopropyl formate concentration in the aqueous phase when no decomposition reagent was added to the aqueous phase, and 2 mL or 6 mL of 10 M HCl was added.

Figure 12:
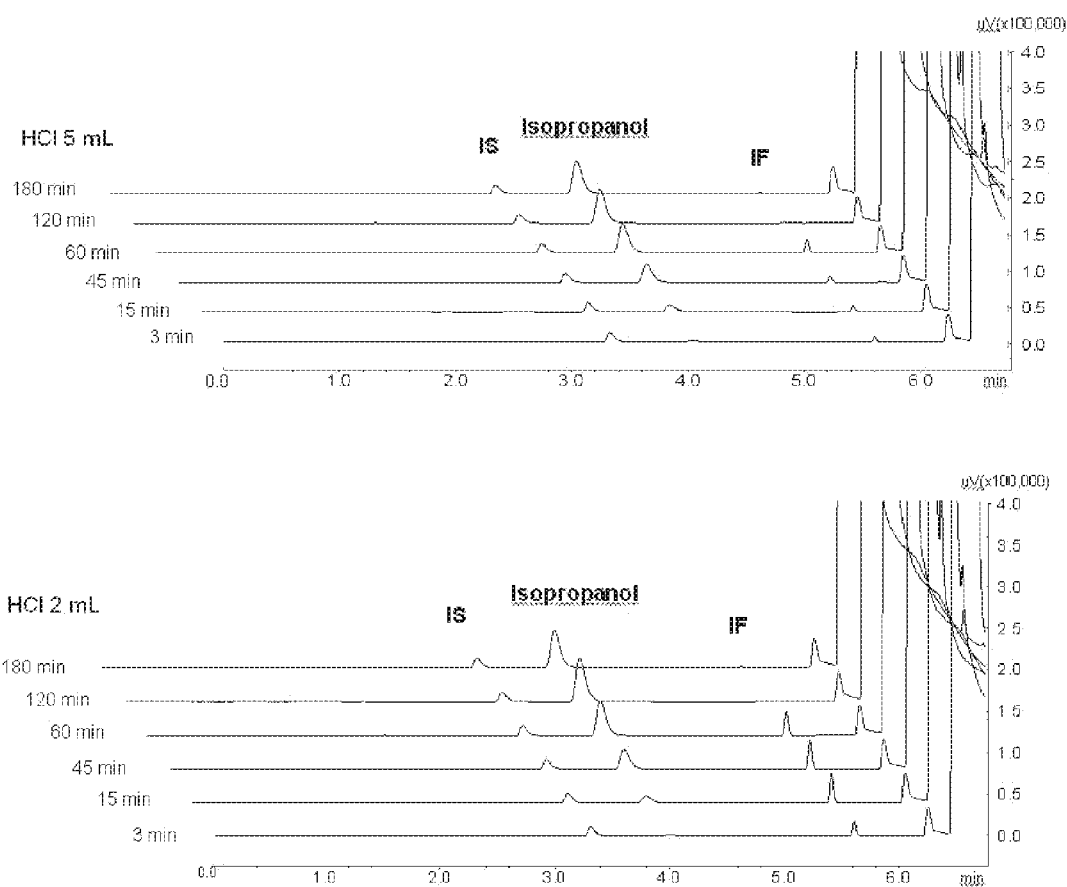
FIG. 12 shows GC chromatograms of an aqueous phase sample depending on time of an isopropyl formate/aqueous phase system following slow stirring.

FIG. 12 shows GC chromatograms of an aqueous phase sample depending on time of an isopropyl formate/aqueous phase system following slow stirring. Each chromatogram is for the case where 2 mL or 5 mL of 10 M HCl was added to the aqueous phase (IF=isopropyl formate, IS=internal standard).

Figure 13:
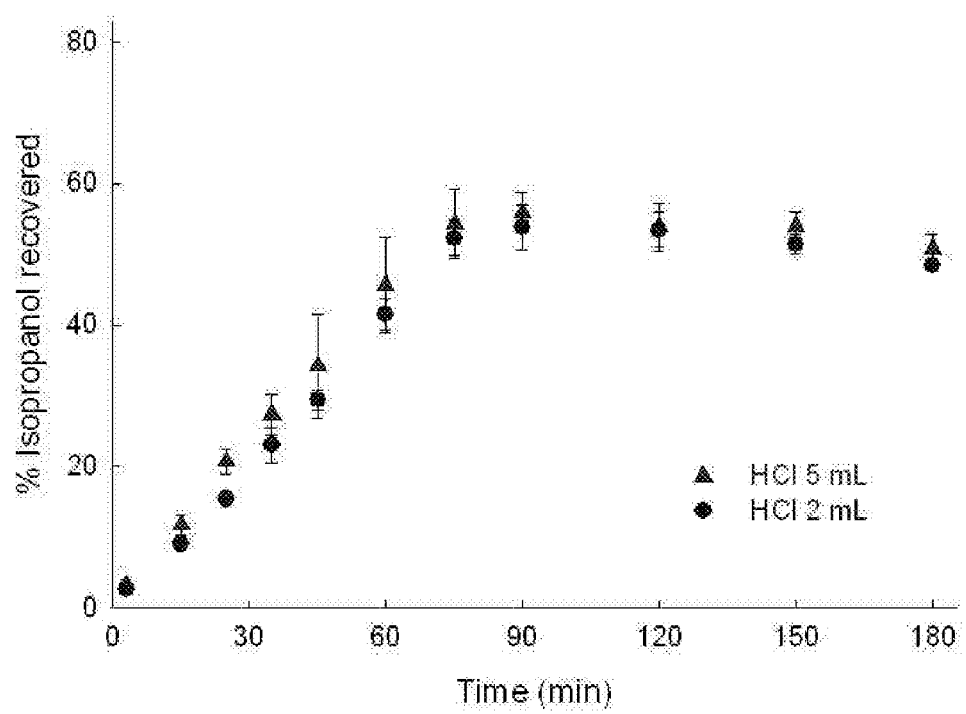
FIG. 13 shows a change of isopropanol concentration in the aqueous phase depending on time.

FIG. 13 shows a change of isopropanol concentration in the aqueous phase. It shows that, when 2 mL or 5 mL of 10 M HCl was added, isopropyl formate was decomposed and changed into isopropanol.

Figure 14:
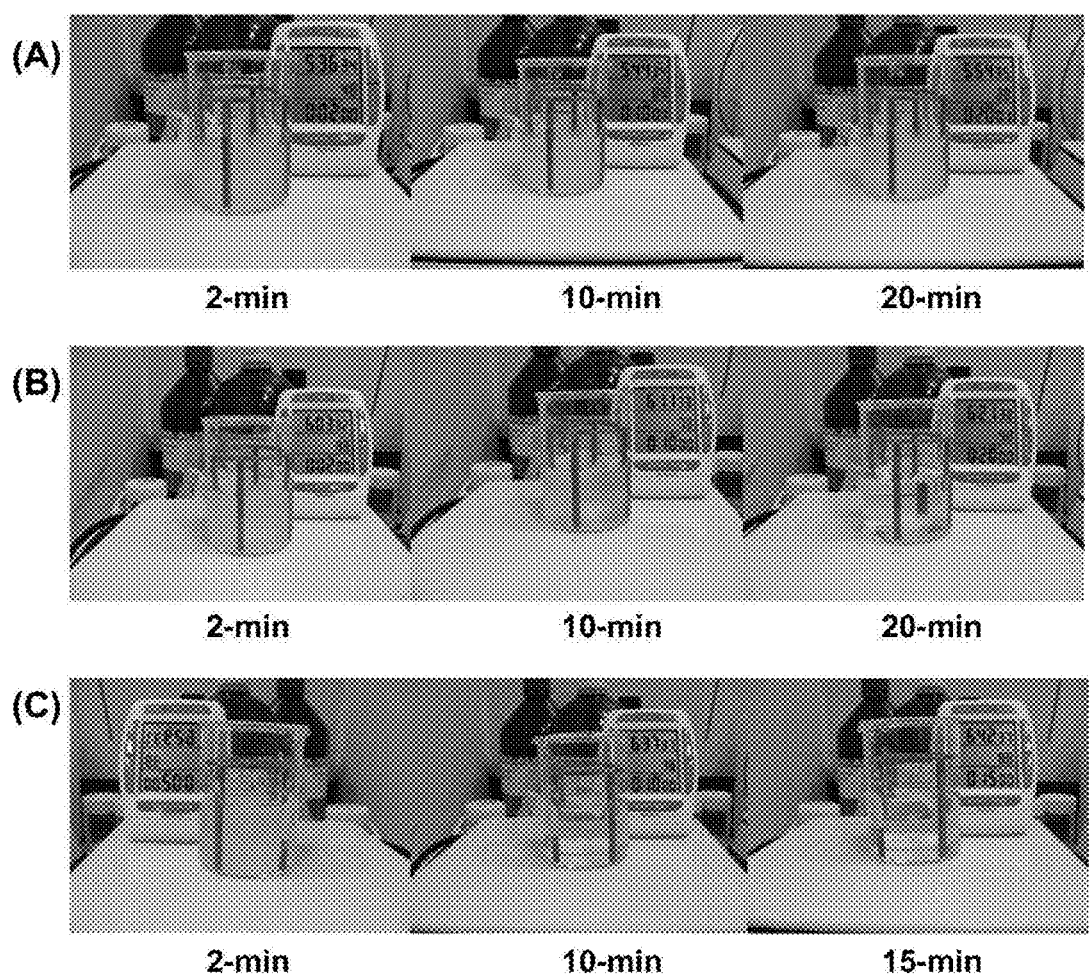
FIG. 14 shows a change of emulsion depending on time when a propionic anhydride/aqueous phase system (A) is stirred without adding an acid or base, (B) is stirred after adding 2 mL of strong HCl, and (C) is stirred after adding 3 mL of 10 M NaOH.

FIG. 14 shows a change of emulsion depending on time when a propionic anhydride/aqueous phase system (A) is stirred without adding an acid or base, (B) is stirred after adding 2 mL of strong HCl, and (C) is stirred after adding 3 mL of 10 M NaOH. When no acid or base was added, two phases were maintained. In contrast, when the acid (B) or the base (C) was added, the emulsion disappeared and a clear and transparent single phase appeared.

Figure 15:
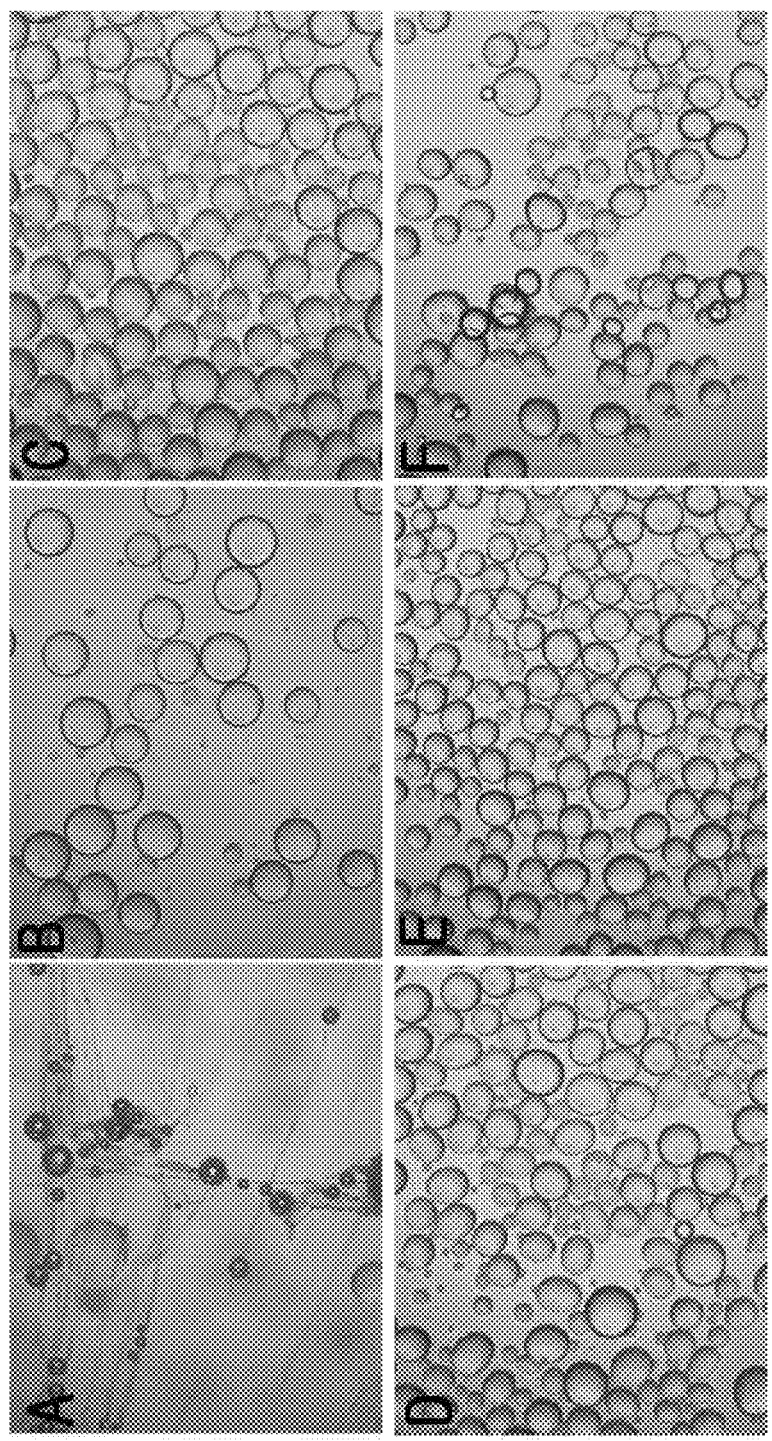
FIG. 15 shows light micrographs of 7E microparticles prepared by using isopropyl formate as an organic solvent and using NaOH at various concentrations as a decomposition reagent. (A): NaOH was not added (0 mL). (B)-(F): 1, 2, 3, 4 and 5 mL of 10 M NaOH was added, respectively.

FIG. 15 shows light micrographs of 7E microparticles prepared by using isopropyl formate as an organic solvent and using NaOH at various concentrations as a decomposition reagent. (A): NaOH was not added (0 mL). (B)-(F): 1, 2, 3, 4 and 5 mL of 10 M NaOH was added, respectively. When NaOH was not added, the emulsion droplets coalesced to form a polymeric film.

Figure 16:
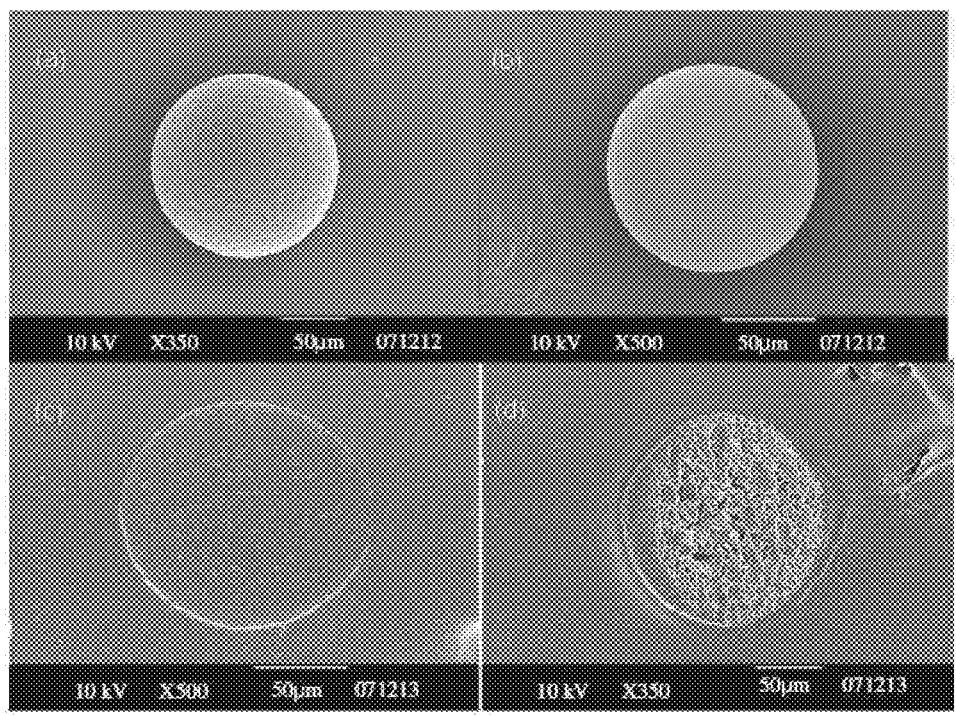
FIG. 16 shows electron micrographs of 7E microparticles prepared by using NaOH as an ethyl acetate decomposition reagent.

FIG. 16 shows electron micrographs of 7E microparticles prepared by using NaOH as an ethyl acetate decomposition reagent. (a), (c): Inside and outside of the microparticles prepared by using 60 mg of progesterone. (b), (d): Inside and outside of the microparticles prepared by using 250 mg of progesterone.

Figure 17:
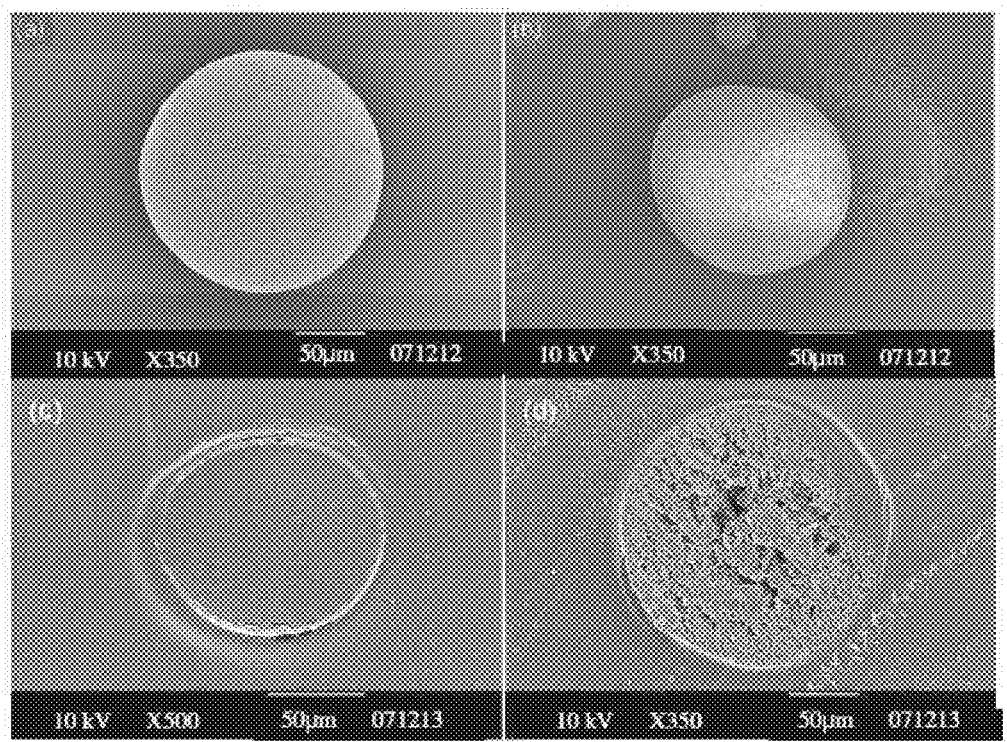
FIG. 17 shows electron micrographs of 7E microparticles prepared by using NaOH as an ethyl formate decomposition reagent.

FIG. 17 shows electron micrographs of 7E microparticles prepared by using NaOH as an ethyl formate decomposition reagent. (a), (c): Inside and outside of the microparticles prepared by using 60 mg of progesterone. (b), (d): Inside and outside of the microparticles prepared by using 250 mg of progesterone.

Figure 18:
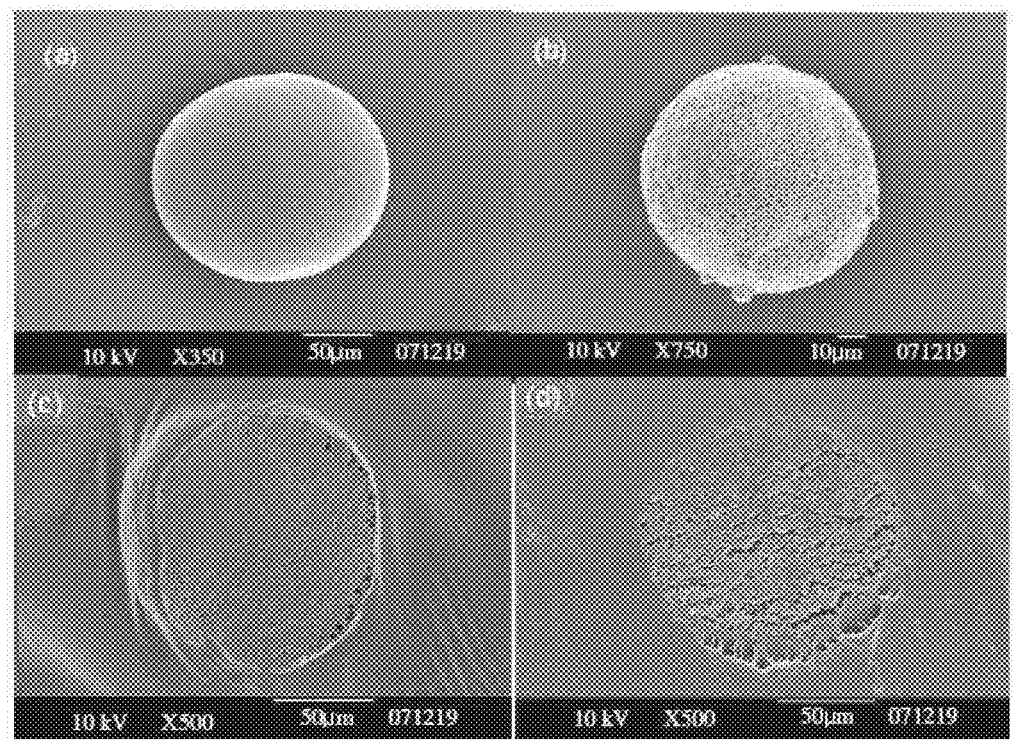
FIG. 18 shows electron micrographs of microparticles prepared by using 0.25 g of 4A PLGA and NaOH as an ethyl acetate decomposition reagent.

FIG. 18 shows electron micrographs of microparticles prepared by using 0.25 g of 4A PLGA and NaOH as an ethyl acetate decomposition reagent. (a), (c): Inside and outside of the microparticles prepared by using 60 mg of progesterone. (b), (d): Inside and outside of the microparticles prepared by using 250 mg of progesterone.

Figure 19:
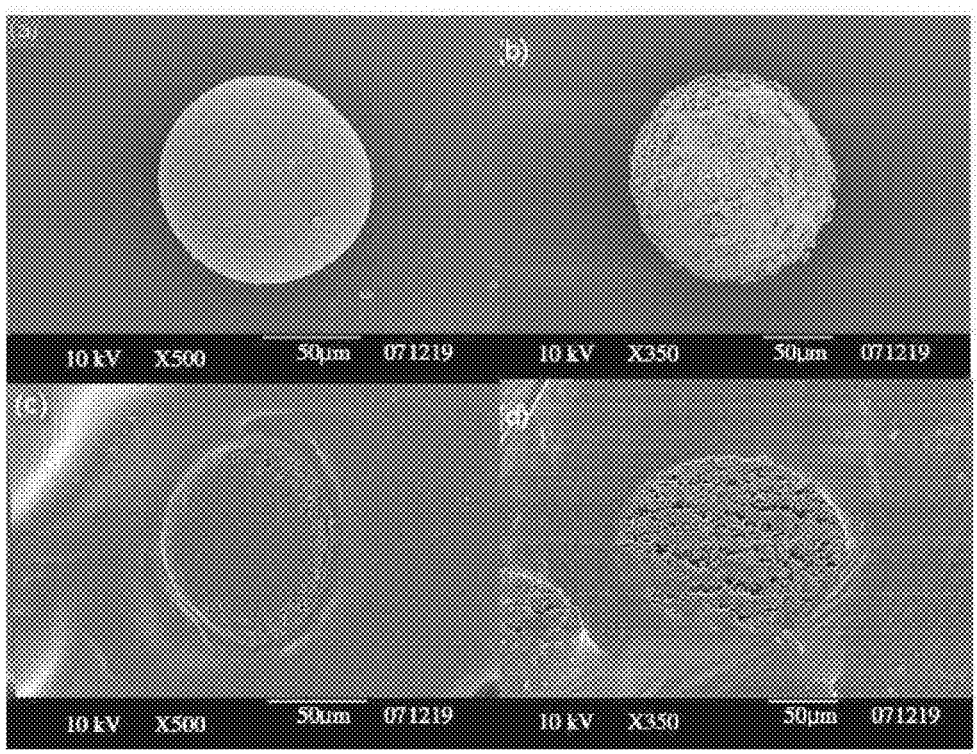
FIG. 19 shows electron micrographs of microparticles prepared by using 0.25 g of 4A PLGA and NaOH as an ethyl formate decomposition reagent.

FIG. 19 shows electron micrographs of microparticles prepared by using 0.25 g of 4A PLGA and NaOH as an ethyl formate decomposition reagent. (a), (c): Inside and outside of the microparticles prepared by using 60 mg of progesterone. (b), (d): Inside and outside of the microparticles prepared by using 250 mg of progesterone.

Figure 20:
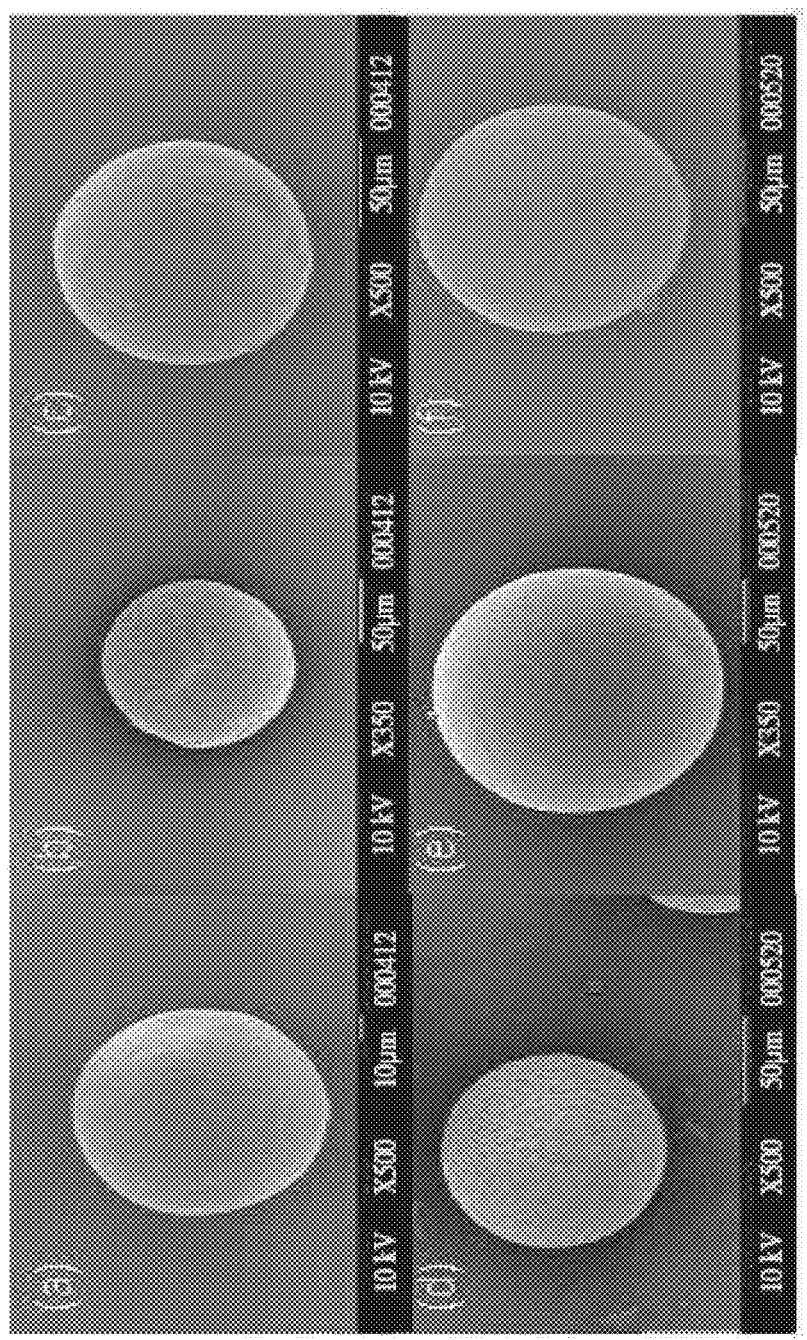
FIG. 20 shows electron micrographs showing outside of microparticles prepared by using 10 M NaOH as an isopropyl formate decomposition reagent.

FIG. 20 shows electron micrographs showing outside of microparticles prepared by using 10 M NaOH as an isopropyl formate decomposition reagent. In (a), (b), (c), (d), (e) and (f), 0, 60, 100, 160, 200 and 250 mg of progesterone was used, respectively.

Figure 21:
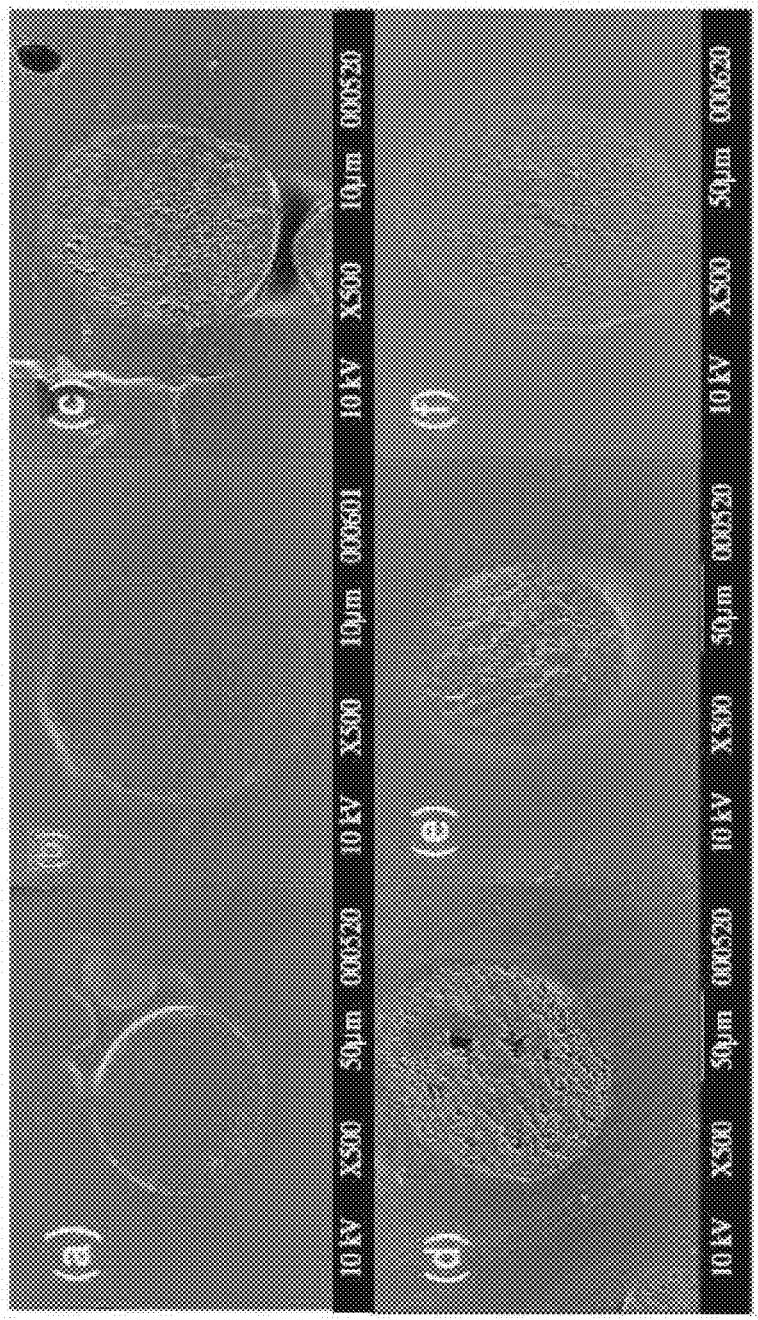
FIG. 21 shows electron micrographs showing inside of microparticles prepared by using 10 M NaOH as an isopropyl formate decomposition reagent.

FIG. 21 shows electron micrographs showing inside of microparticles prepared by using 10 M NaOH as an isopropyl formate decomposition reagent. In (a), (b), (c), (d), (e) and (f), 0, 60, 100, 160, 200 and 250 mg of progesterone was used, respectively.

Figure 22:
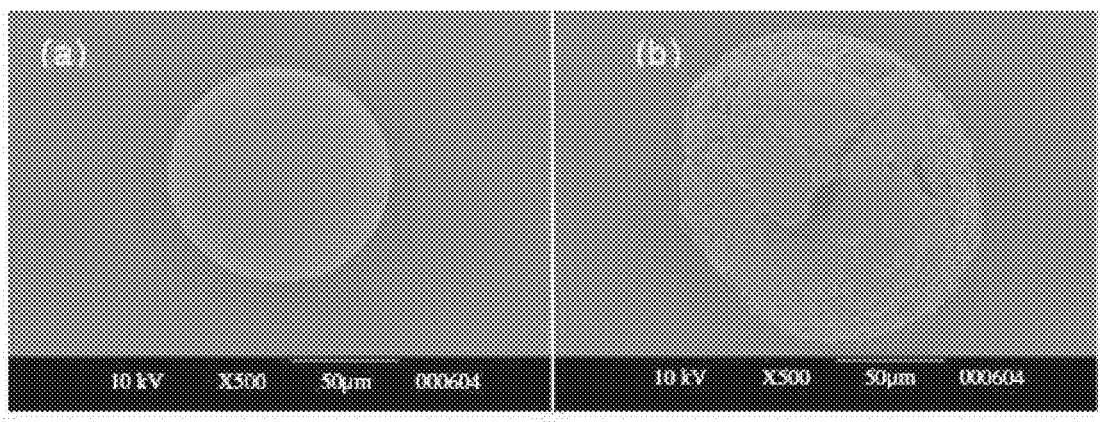
FIG. 22 shows electron micrographs of microparticles prepared by using propyl formate as an organic solvent and 2 mL of HCl as a decomposition reagent.

FIG. 22 shows electron micrographs of microparticles prepared by using propyl formate as an organic solvent and 2 mL of HCl as a decomposition reagent. (a): Microparticles prepared by using 0.25 g of 7E polymer only. (b): Microparticles prepared by using 0.25 g of 7E polymer and 250 mg of progesterone.

Figure 23:
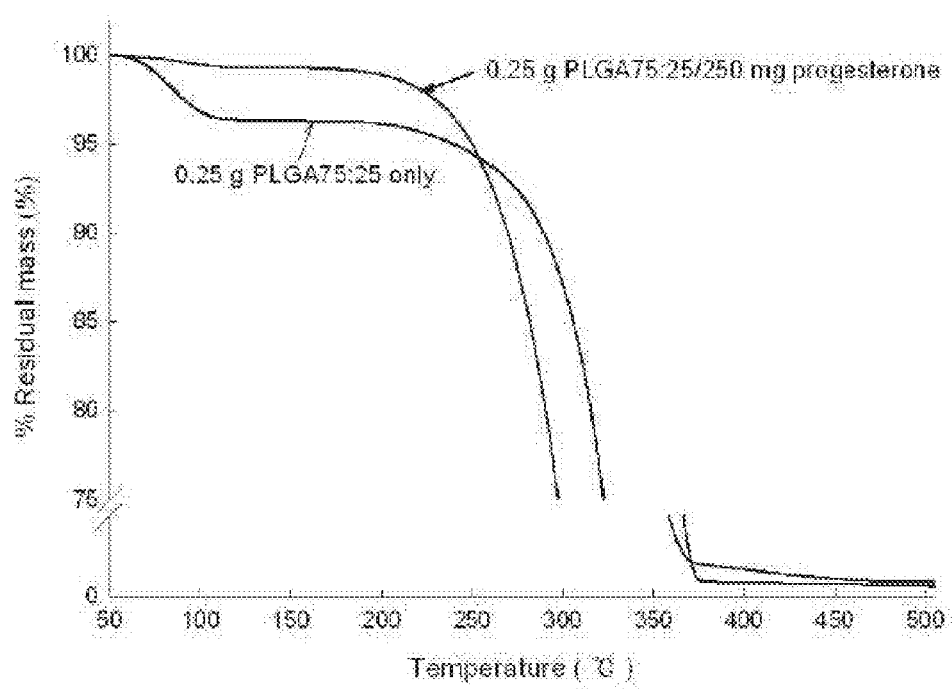
FIG. 23 shows a thermogravimetric analysis result of microparticle samples.

FIG. 23 shows a thermogravimetric analysis result of microparticle samples. It can be seen that the amount of the volatile residual organic solvent is extremely slight in the microparticles comprising progesterone, and is smaller than that of the microparticles not containing progesterone.

Figure 24:
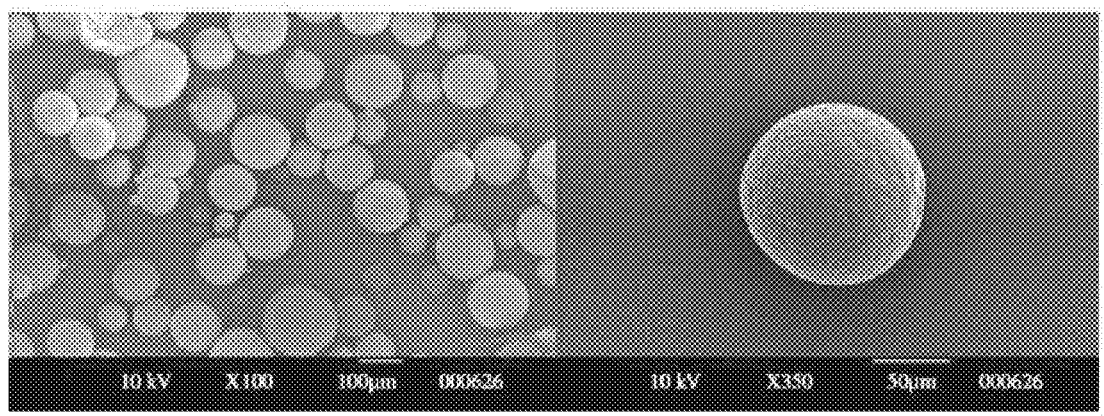
FIG. 24 shows electron micrographs of microparticles prepared by using 60 mg of anastrazole, 0.15 g of 7E, 0.1 g of 4A and NaOH as an ethyl acetate decomposition reagent.

FIG. 24 shows electron micrographs of microparticles prepared by using 60 mg of anastrazole, 0.15 g of 7E, 0.1 g of 4A and NaOH as an ethyl acetate decomposition reagent.

Figure 25:
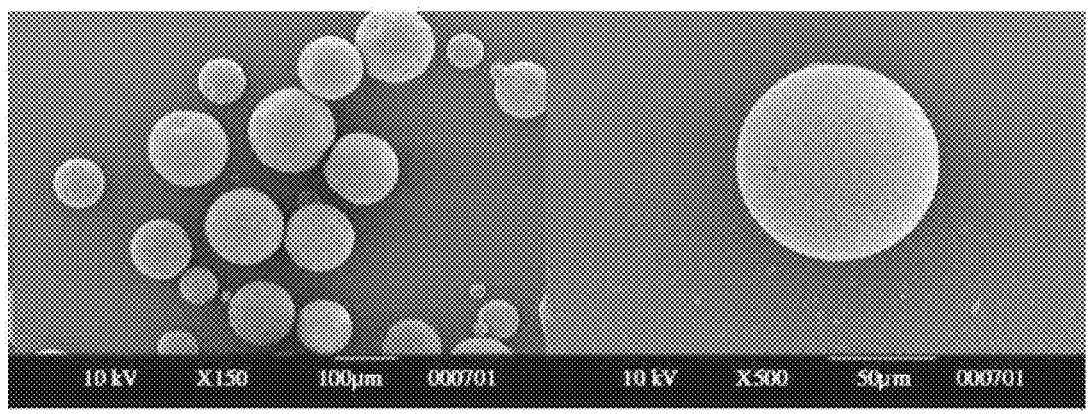
FIG. 25 shows electron micrographs of microparticles prepared by using 60 mg of anastrazole, 0.15 g of 7E, 0.1 g of 4A and NaOH as an ethyl formate decomposition reagent.

FIG. 25 shows electron micrographs of microparticles prepared by using 60 mg of anastrazole, 0.15 g of 7E, 0.1 g of 4A and NaOH as an ethyl formate decomposition reagent.

Figure 26:
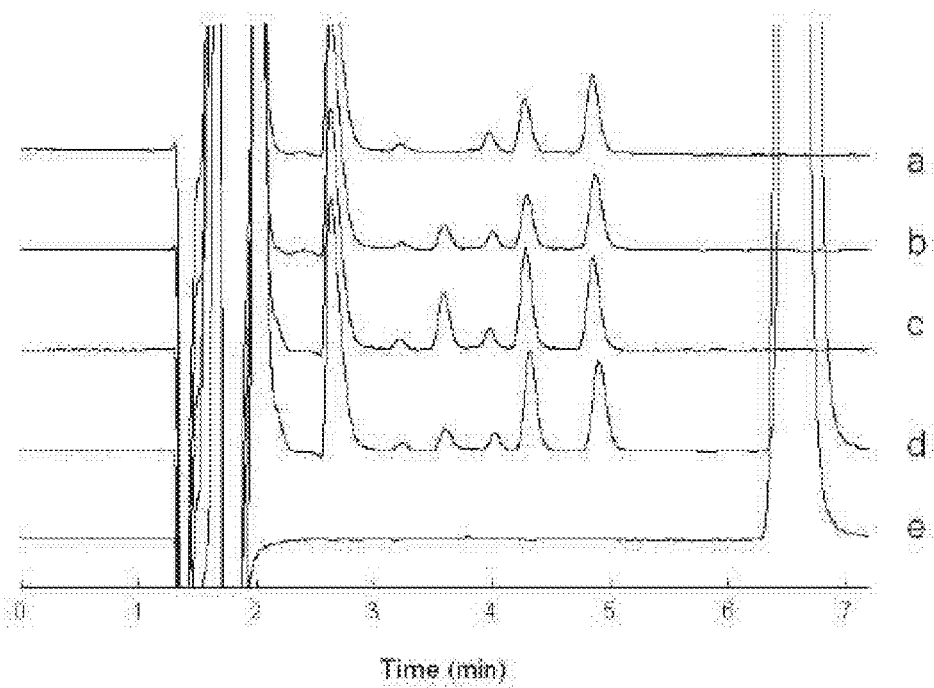
FIG. 26 shows HPLC chromatograms of various samples under an anastrazole encapsulation ratio analysis condition.

FIG. 26 shows HPLC chromatograms of various samples under an anastrazole encapsulation ratio analysis condition. (a): Mixture solution of tetrahydrofuran and 50% acetonitrile aqueous solution. (b): Solution prepared by spiking ethyl acetate in sample (a). (c): Filtrate by an experimental condition of blank microparticles not containing drug. (d) Filtrate by an experimental condition of microparticles containing anastrazole. (e): Anastrazole standard solution prepared by using 50% acetonitrile aqueous solution. It can be seen that a very small amount of ethyl acetate is detected from the two microparticle samples and no anastrazole modification product is detected.

Figure 27:
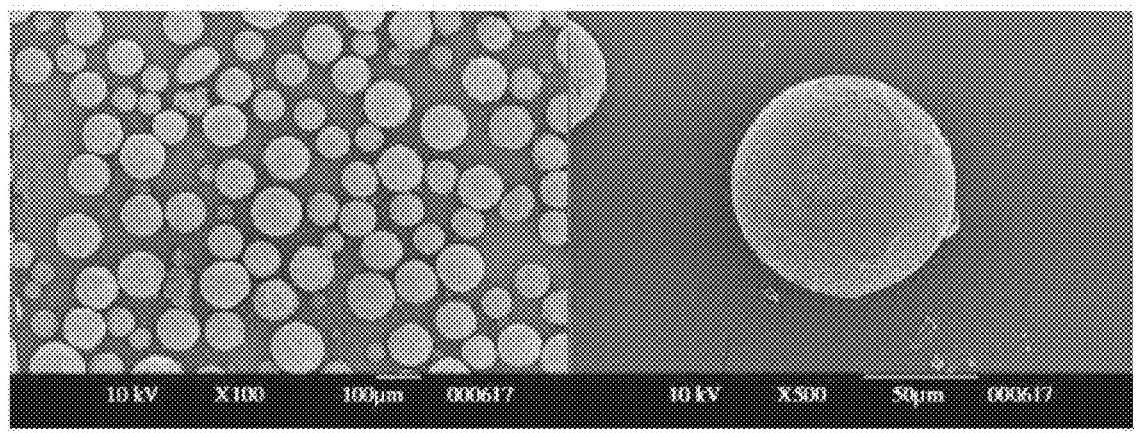
FIG. 27 shows electron micrographs of microparticles prepared by using 60 mg of olanzapine, 0.15 g of 7E, 0.1 g of 4A and NaOH as an ethyl acetate decomposition reagent.

FIG. 27 shows electron micrographs of microparticles prepared by using 60 mg of olanzapine, 0.15 g of 7E, 0.1 g of 4A and NaOH as an ethyl acetate decomposition reagent.

Figure 28:
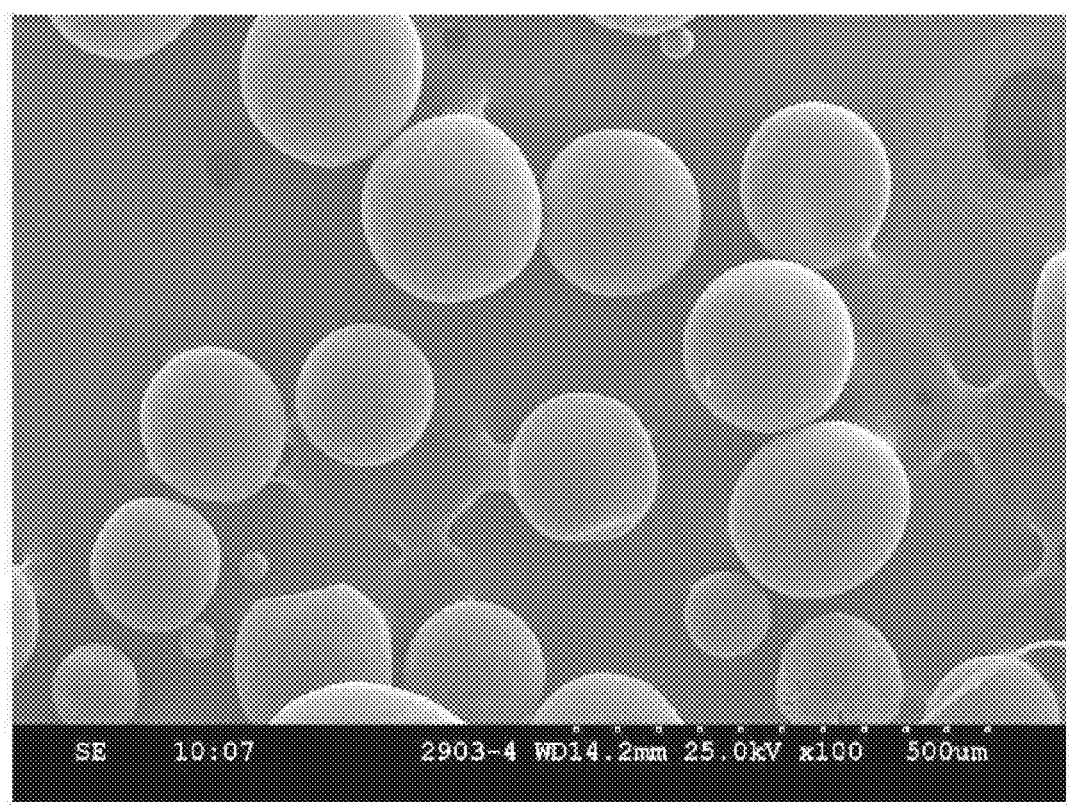
FIG. 28 shows electron micrographs of microparticles prepared by using 60 mg of risperidone, 0.25 g of 4A and NaOH as an ethyl acetate decomposition reagent.

FIG. 28 shows electron micrographs of microparticles prepared by using 60 mg of risperidone, 0.25 g of 4A and NaOH as an ethyl formate decomposition reagent.

Figure 29:
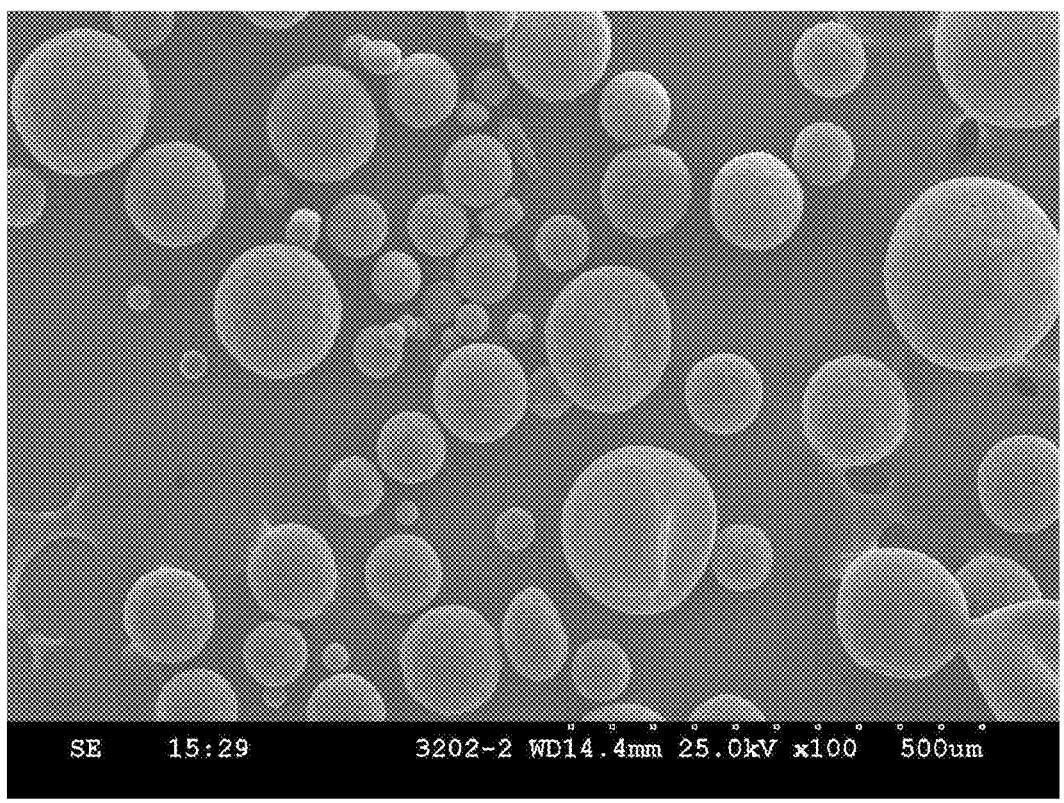
FIG. 29 shows electron micrographs of microparticles prepared by using 40 mg of aripiprazole, 0.25 g of 4A and NaOH as an ethyl acetate decomposition reagent.

FIG. 29 shows electron micrographs of microparticles prepared by using 40 mg of aripiprazole, 0.25 g of 4A and NaOH as an ethyl formate decomposition reagent.

The following examples are for illustrative purposes only and not intended to limit the scope of the present invention.

EXAMPLE

Example 1

Removal of Organic Solvent (Ethyl Acetate) Using Acid or Base

It was investigated whether ethyl acetate is decomposed and removed by an acid or a base. When ethyl acetate is decomposed by an acid or a base, water-soluble ethanol and acetic acid are produced. Therefore, concentrations of ethyl acetate and ethanol in the aqueous solution were quantitated by gas chromatography (GC).

40 mL of 0.5% polyvinyl alcohol (PVA) aqueous solution was added to a beaker. After adding 2 mL or 5 mL of 10 M NaOH or 10 M HCl (0 mL for the blank), 4 mL of ethyl acetate was added along the wall. While stirring such that the two phases are not completely mixed, each 200 of sample was taken from the aqueous phase at 3, 15, 25, 35, 45, 60 and 75 minutes for GC analysis.

GC analysis was performed with GC-2010 (Shimadzu, Japan). Zebron ZB-624 (Phenomenex, USA) analysis column using 6%-cyanopropylphenyl-94%-methylpolysiloxane as stationary phase was used. The quantity of ethyl acetate, and ethanol which is the decomposition products of ethyl acetate, was measured using isopropanol as internal standard.

As seen in FIG. 1 and FIG. 2, when no reagent was added to the aqueous phase (blank), some of ethyl acetate was changed to the aqueous phase with time. Its concentration in the aqueous phase increased until it reached a constant value. This means that ethyl acetate was saturated in the aqueous phase. In addition, ethanol was not detected at all in the aqueous phase because ethyl acetate was not decomposed.

In contrast, when 5 mL of 10 M NaOH was added, the concentration of ethanol, which is the hydrolysis product of ethyl acetate, continued to increase. This is because ethanol and sodium acetate are produced as ethyl acetate is hydrolyzed. Further, ethyl acetate dissolved in the aqueous phase was not detected because it was quickly decomposed by NaOH. Upon completion of the reaction, the two phases were completely mixed into one phase.

When 2 mL of 10 M NaOH was added, initially, ethanol was produced as ethyl acetate was decomposed. However, when NaOH was consumed after time passed, ethanol did not increase any more and ethyl acetate dissolved in the aqueous phase was detected.

Example 2

Removal of Organic Solvent (Ethyl Formate) Using Acid or Base

It was investigated whether ethyl formate is decomposed and removed by an acid or a base. When ethyl formate is decomposed by an acid or a base, water-soluble ethanol and formic acid are produced. Therefore, concentrations of ethyl formate and ethanol in the aqueous solution were quantitated by gas chromatography (GC).

40 mL of 0.5% polyvinyl alcohol (PVA) aqueous solution was added to a beaker. After adding 2 mL or 6 mL of 10 M NaOH or 10 M HCl (0 mL for the blank), 4 mL of ethyl formate was added along the wall. Stirring was performed such that the two phases are not completely mixed, so that some of ethyl formate diffused into the aqueous phase. Each 200 of sample was taken from the aqueous phase at 5, 10, 15, 20, 30, 45 and 60 minutes for GC analysis.

GC analysis was performed with GC-2010 (Shimadzu, Japan). Zebron ZB-624 (Phenomenex, USA) analysis column using 6%-cyanopropylphenyl-94%-methylpolysiloxane as stationary phase was used. The quantity of ethyl formate, and ethanol which is the decomposition products of ethyl formate, was measured using methanol as internal standard.

As seen in FIG. 3 and FIG. 4, when no reagent was added to the aqueous phase, some of ethyl formate was changed into the aqueous phase with time. Its concentration in the aqueous phase increased until it reached a constant value. This means that ethyl formate was saturated in the aqueous phase. In addition, ethanol was not detected at all in the aqueous phase because ethyl formate was not decomposed.

In contrast, when 6 mL of 10 M NaOH was added, the concentration of ethanol, which is the hydrolysis product of ethyl formate, continued to increase. This is because ethanol and sodium formate are produced as ethyl formate is hydrolyzed. Further, ethyl formate dissolved in the aqueous phase was not detected because it was quickly decomposed by NaOH. Upon completion of the reaction, the two phases were completely mixed into one phase.

When 2 mL of 10 M NaOH was added, initially, ethanol was produced as ethyl formate was decomposed. However, as time passed and NaOH was consumed, ethanol did not increase any more and ethyl formate dissolved in the aqueous phase was detected.

When 10 M HCl was used as an ethyl formate decomposition reagent instead of 10M NaOH, as seen in FIG. 4 and FIG. 5B, ethyl formate was effectively decomposed in both cases where 6 mL and 2 mL of HCl were used when the reaction time is prolonged. This is because, whereas NaOH is consumed during the reaction, HCl acts as a catalyst without being consumed.

Example 3

Removal of Organic Solvent (Propyl Formate) Using Acid or Base

It was investigated whether propyl formate is decomposed and removed by an acid or a base. When ethyl formate is decomposed by an acid or a base, water-soluble propanol and formic acid are produced. Therefore, concentrations of propyl formate and propanol in the aqueous solution were quantitated by gas chromatography (GC).

40 mL of 0.5% polyvinyl alcohol (PVA) aqueous solution was added to a beaker. After adding 2 mL or 6 mL of 10 M NaOH or 10 M HCl (0 mL for the blank), 4 mL of propyl formate was added along the wall. Stirring was performed such that the two phases are not completely mixed, so that some of ethyl formate diffused into the aqueous phase. Each 200 of sample was taken from the aqueous phase at 5, 10, 15, 20, 30, 45, 60, 85, 120 and 160 minutes for GC analysis.

GC analysis was performed with GC-2010 (Shimadzu, Japan). Zebron ZB-624 (Phenomenex, USA) analysis column using 6%-cyanopropylphenyl-94%-methylpolysiloxane as stationary phase was used. The quantity of propyl formate, and propanol which is the decomposition products of propyl formate, was measured using ethanol as internal standard.

As seen in FIG. 6 and FIG. 7, when no reagent was added to the aqueous phase, some of propyl formate was transported into the aqueous phase with time. Its concentration in the aqueous phase increased until it reached a constant value. This means that propyl formate was saturated in the aqueous phase. In addition, propanol was not detected at all in the aqueous phase because propyl formate was not decomposed.

In contrast, when 5 mL of 10 M NaOH was added, the concentration of propanol, which is the hydrolysis product of propyl formate, continued to increase. This is because propanol and sodium formate are produced as propyl formate is hydrolyzed. Further, propyl formate dissolved in the aqueous phase was not detected because it was quickly decomposed by NaOH. Upon completion of the reaction, the two phases were completely mixed into one phase.

When 2 mL of 10 M NaOH was added, initially, ethanol was produced as propyl formate was decomposed. However, as time passed and NaOH was consumed, propanol did not increase any more and propyl formate dissolved in the aqueous phase was detected.

When 10 M HCl was used as a propyl formate decomposition reagent instead of 10 M NaOH, as seen in FIG. 8 and FIG. 9, propyl formate was effectively decomposed in both cases where 6 mL and 2 mL of HCl was used when the reaction time is prolonged. This is because, whereas NaOH is consumed during the reaction, HCl acts as a catalyst without being consumed.

Example 4

Removal of Organic Solvent (Isopropyl Formate) Using Acid or Base

It was investigated whether isopropyl formate is decomposed and removed by an acid or a base. When isopropyl formate is decomposed by an acid or a base, water-soluble isopropanol and formic acid are produced. Therefore, concentrations of isopropyl formate and isopropanol in the aqueous solution were quantitated by gas chromatography (GC).

40 mL of 0.5% polyvinyl alcohol aqueous solution was added to a beaker. After adding 2 mL or 5 mL of 10 M NaOH or 10 M HCl (0 mL for the blank), 4 mL of isopropyl formate was added. While stirring such that the two phases are not completely mixed, so each 200 of sample was taken from the aqueous phase at 3, 15, 25, 35, 45, 60, 75, 90, 120, 150 and 180 minutes for GC analysis.

GC analysis was performed with GC-2010 (Shimadzu, Japan). Zebron ZB-624 (Phenomenex, USA) analysis column using 6%-cyanopropylphenyl-94%-methylpolysiloxane as stationary phase was used. The quantity of isopropyl formate, and isopropanol which is the decomposition products of isopropyl formate, was measured using ethanol as internal standard.

As seen in FIG. 10 and FIG. 11, when no reagent was added to the aqueous phase, some of isopropyl formate was transferred to the aqueous phase with time. Its concentration increased until it reached a constant value. This means that isopropyl formate was saturated in the aqueous phase. In addition, isopropanol was not detected at all in the aqueous phase because isopropyl formate was not decomposed.

In contrast, when 5 mL of 10 M NaOH was added, the concentration of isopropanol, which is the hydrolysis product of isopropyl formate, continued to increase. This is because isopropanol and sodium formate are produced as isopropyl formate is hydrolyzed. Further, isopropyl formate dissolved in the aqueous phase was not detected because it was quickly decomposed by NaOH. Upon completion of the reaction, the two phases were completely mixed into one phase.

When 2 mL of 10 M NaOH was added, initially, ethanol was produced as isopropyl formate was decomposed. However, as time passed and NaOH was consumed, isopropanol did not increase any more and isopropyl formate dissolved in the aqueous phase was detected.

When 10 M HCl was used as a isopropyl formate decomposition reagent instead of 10 M NaOH, as seen in FIG. 12 and FIG. 13, isopropyl formate was effectively decomposed in both the cases where 6 mL and 2 mL of HCl was used when the reaction time is prolonged. This is because, whereas NaOH is consumed during the reaction, HCl acts as a catalyst without being consumed.

Example 5

Removal of Organic Solvent (Propionic Anhydride) Using Acid or Base

It was investigated whether propionic anhydride is hydrolyzed by an acid or a base. When propionic anhydride is decomposed by an acid or a base, water-soluble propionic acid is produced. Therefore, we confirmed whether the initial two phases were completely mixed into one phase upon completion of the reaction.

40 mL of 0.5% polyvinyl alcohol aqueous solution was added to a beaker. After adding 3 mL of 10 M NaOH (or 2 mL of strong HCl), the stirring speed of the stirrer was set at 550 rpm. After adding 4 mL of propionic anhydride, change of phase was observed with time. For control experiment, 4 mL of propionic anhydride was emulsified in 40 mL of 0.5% polyvinyl alcohol aqueous solution without adding NaOH or HCl, and change of phase was observed.

As seen in FIG. 14, when an acid or a base was not added, the hazy emulsion state (actually, two phases) was maintained even after stirring for 20 minutes. This means that the aqueous phase is quickly saturated with some of the propionic anhydride, and the remaining propionic anhydride persists in the emulsion droplets. However, when an acid or a base was added, the emulsion disappeared within 20 minutes and a clear and transparent single phase appeared. This result shows that the water-insoluble propionic anhydride was completely converted into water-soluble propionic acid through acid/base reaction.

Example 6

Hardening of Microparticles Depending on the Amount of Organic Solvent Decomposition Reagent The polymer used Example 6 to Example 12 in the present invention is poly-d,l-lactide-co-glycolide (PLGA), specifically, PLGA 75:25 (i.v.=0.70 dL/g in CHCl$_3$, its abbreviation refers to 7E), PLGA 50:50(i.v.=0.46 dL/g in CHCl$_3$, its abbreviation refers to 4A), and PLGA 50:50(i.v.=0.18 dL/g in CHCl$_3$, its abbreviation refers to 2A).

0.25 g of 7E was completely dissolved in 4 mL of isopropyl formate. The resultant dispersed phase was added to a beaker containing 40 mL of 0.5% polyvinyl alcohol aqueous solution and emulsified by stirrer. The resultant emulsion was stirred for 3 minutes and, after adding 0, 1, 2, 3, 4 and 5 mL of 10 M NaOH, further stirred for 15 minutes. Then, some of the sample was taken and observed on a glass slide using an optical microscope.

As seen in FIG. 15, when isopropyl formate was used as an organic solvent, the emulsion droplets remained in the liquid state for 15 minutes when no NaOH was used. Therefore, when stirring was stopped and the sample was placed on the glass slide for optical microscope imaging, the emulsion droplets coalesced into film-shaped aggregates, not microparticles. In contrast, when 1 mL of 10M NaOH was added, the emulsion droplets did not coalesce. Similarly, when 2 mL to 5 mL of NaOH were added, the coalescence of the emulsion droplets could be effectively prevented.

Example 7

Preparation of Microparticles Encapsulating Progesterone

<7-1> Preparation of Microparticles Encapsulating Progesterone Using Ethyl Acetate or Ethyl Formate 0.25 g of 7E or 4A was dissolved in 4 mL of ethyl acetate. After adding and dissolving progesterone (60 or 250 mg) therein, the resultant dispersed phase was added to 40 mL of 0.5% polyvinyl alcohol (PVA) aqueous solution and stirred to prepare an oil-in-water (o/w) emulsion. After adding 5 mL of 10 M NaOH to the emulsion, followed by reaction for 30 minutes, 40 mL of distilled water was added. After stirring and filtration, microparticles were recovered. The microparticles were redispersed in 16 mL of 0.5% PVA solution and stirred, after adding distilled water to make 80 mL. After filtration, the microparticles were dried overnight in a vacuum dryer.

Similarly, microparticles encapsulating progesterone were prepared using ethyl formate instead of ethyl acetate and using 6 mL of 10 M NaOH or 5 mL of 10 M HCl as a decomposition reagent.

As seen in FIG. 16, FIG. 17, FIG. 18 and FIG. 19, microspheres encapsulating progesterone were prepared well. When ethyl acetate or ethyl formate was used as an organic solvent, inside and outside shapes of the microparticles were similar.

<7-2> Measurement of Progesterone Encapsulation Ratio

Some of the microparticles prepared in Example <7-1> were accurately weighed and dissolved in 4 mL of tetrahydrofuran. After diluting 6 times with methanol, the solution was filtered to remove the PLGA precipitate. Some of the filtrate (20 μl) was subjected to HPLC (Shimadzu LC-20AD, Luna 5 m C18(2) column) for measurement of progesterone concentration. Theoretical drug load (%) and actual drug load (%) were calculated from the following equations, and their ratio was defined as drug encapsulation ratio (%).

Theoretical drug load (%)=(Weight of drug used (mg)/
[Weight of PLGA used (mg)+Weight of drug used (mg)])×100

Actual drug load (%)=(Weight of drug encapsulated in microparticles (mg)/Weight of microparticles used for encapsulation ratio measurement (mg))×100

Drug encapsulation ratio (%)=(Actual drug load (%)/Theoretical drug load (%))×100

As seen in Table 1 (ethyl acetate) and Table 2 (ethyl formate), most of the added progesterone was encapsulated in the microparticles. The difference in the used organic solvent did not result in a significant difference of progesterone encapsulation ratio. When ethyl formate was used, similar encapsulation ratio was attained with 10 M NaOH and 10 M HCl. All the experiments exhibited batch reproducibility, with similar encapsulation ratios between batches.

TABLE 1

| PLGA/ quantity | Progesterone (mg) | Decomposition reagent | Encapsulation ratio (%) | | |
|---|---|---|---|---|---|
| | | | Batch 1 | Batch 2 | Batch 3 |
| 7E/0.25 g | 60 | 10M NaOH 5 mL | 93.8 | 92.3 | 96.0 |
| 7E/0.25 g | 250 | 10M NaOH 5 mL | 92.8 | 92.0 | 97.7 |
| 4A/0.25 g | 60 | 10M NaOH 5 mL | 90.5 | 92.8 | 95.3 |
| 4A/0.25 g | 250 | 10M NaOH 5 mL | 93.2 | 92.2 | 98.5 |

TABLE 2

| PLGA/ quantity | Progesterone (mg) | Decomposition reagent | Encapsulation ratio (%) | | |
|---|---|---|---|---|---|
| | | | Batch 1 | Batch 2 | Batch 3 |
| 7E/0.25 g | 60 | 10M NaOH 6 mL | 93.9 | 94.0 | 91.6 |
| 7E/0.25 g | 250 | 10M NaOH 6 mL | 95.5 | 98.5 | 99.7 |
| 4A/0.25 g | 60 | 10M NaOH 6 mL | 92.0 | 93.3 | 95.6 |
| 4A/0.25 g | 250 | 10M NaOH 6 mL | 96.2 | 93.2 | 100.7 |
| 7E/0.25 g | 60 | 10M HCl 5 mL | 84.1 | 88.7 | 86.1 |
| 7E/0.25 g | 100 | 10M HCl 5 mL | 89.0 | 92.8 | 91.5 |
| 7E/0.25 g | 160 | 10M HCl 5 mL | 98.9 | 102.0 | 96.9 |

TABLE 2-continued

| PLGA/ quantity | Progesterone (mg) | Decomposition reagent | Encapsulation ratio (%) | | |
|---|---|---|---|---|---|
| | | | Batch 1 | Batch 2 | Batch 3 |
| 7E/0.25 g | 200 | 10M HCl 5 mL | 99.2 | 102.0 | 95.5 |
| 7E/0.25 g | 250 | 10M HCl 5 mL | 101.0 | 101.0 | 99.6 |

<7-3> Preparation of Microparticles Encapsulating Progesterone Using Propyl Formate or Isopropyl Formate 0.25 g of 7E was dissolved in 4 mL of isopropyl formate or propyl formate. After adding and dissolving progesterone (60 or 250 mg) therein, the resultant dispersed phase was added to 40 mL of 0.5% PVA aqueous solution and stirred to prepare an o/w emulsion. After adding 4 mL of 10 M NaOH to the emulsion, followed by reaction for 30 minutes, 40 mL of distilled water was added. After stirring and filtration, microparticles were recovered. The microparticles were redispersed in 16 mL of 0.5% PVA solution and stirred, after adding distilled water to make 80 mL. After filtration, the microparticles were in a vacuum dryer.

As seen in FIG. 20, FIG. 21 and FIG. 22, when isopropyl formate or propyl formate were used, microspheres encapsulating progesterone were prepared well.

<7-4> Measurement of Progesterone Encapsulation Ratio

Progesterone encapsulation ratio of the microparticles prepared in Example <7-3> was measured as in Example <7-2>.

As seen in Table 3 (propyl formate) and Table 4 (isopropyl formate), most of the added progesterone was encapsulated in the microparticles. The difference in the used organic solvent or the amount of progesterone did not result in a significant difference of progesterone encapsulation ratio.

TABLE 3

| PLGA/ quantity | Progesterone (mg) | Decomposition reagent | Encapsulation ratio (%) |
|---|---|---|---|
| 7E/0.25 g | 60 | 10M NaOH 4 mL | 90.9 ⊚ 2.1 |
| 7E/0.25 g | 100 | 10M NaOH 4 mL | 89.9 ⊚ 1.2 |
| 7E/0.25 g | 160 | 10M NaOH 4 mL | 93.0 ⊚ 1.2 |
| 7E/0.25 g | 200 | 10M NaOH 4 mL | 91.9 ⊚ 1.2 |
| 7E/0.25 g | 250 | 10M NaOH 4 mL | 93.0 ⊚ 1.3 |
| 7E/0.25 g | 60 | 10M HCl 2 mL | 83.5 ⊚ 0.9 |
| 7E/0.25 g | 250 | 10M HCl 2 mL | 95.3 ⊚ 0.9 |

TABLE 4

| PLGA/ quantity | Progesterone (mg) | Decomposition reagent | Encapsulation ratio (%) |
|---|---|---|---|
| 7E/0.25 g | 60 | 10M NaOH 4 mL | 94.6 ⊚ 2.4 |
| 7E/0.25 g | 100 | 10M NaOH 4 mL | 92.4 ⊚ 2.0 |
| 7E/0.25 g | 160 | 10M NaOH 4 mL | 95.4 ⊚ 0.9 |
| 7E/0.25 g | 200 | 10M NaOH 4 mL | 96.1 ⊚ 0.9 |
| 7E/0.25 g | 250 | 10M NaOH 4 mL | 97.5 ⊚ 2.5 |
| 7E/0.25 g | 60 | 10M HCl 2 mL | 83.0 ⊚ 2.1 |
| 7E/0.25 g | 250 | 10M HCl 2 mL | 92.0 ⊚ 2.6 |

<7-5> Measurement of Organic Solvent Remaining in Microparticles

The microparticles prepared using isopropyl formate as an organic solvent in Example <7-3> were stored for 3 days in vacuum state and the quantity of isopropyl formate remaining in the microparticle was measured.

The microparticles (about 30 mg) were accurately weighed and completely dissolved in 2 mL of methylene chloride. After diluting 5 times with butanol, the precipitated PLGA was removed by filtration. The concentration of isopropyl formate in the filtrate was measured by GC analysis in the same manner as in Example 4.

As seen in Table 5, the microparticles prepared in the present invention showed very low residual content of isopropyl formate. This demonstrates that the method for preparing microparticles according to the present invention is remarkably effective in removing the organic solvent since the isopropyl formate transferred from the emulsion droplets to the aqueous phase is effectively and continuously decomposed and removed. The residual content of the solvent was inversely proportional to the quantity of progesterone encapsulated in the microparticles.

TABLE 5

| PLGA/ quantity | Progesterone (mg) | Decomposition reagent | Residual content (%) |
|---|---|---|---|
| 7E/0.25 g | 0 | 10M NaOH 5 mL | 3.15 ⊚ .66 |
| 7E/0.25 g | 60 | 10M NaOH 5 mL | 1.57 ⊚ .46 |
| 7E/0.25 g | 160 | 10M NaOH 5 mL | 1.04 ⊚ 0.16 |
| 7E/0.25 g | 250 | 10M NaOH 5 mL | 0.62 ⊚ 0.07 |

<7-6> Thermogravimetric Analysis of Microparticles

The microparticles prepared in Example <7-3> (using isopropyl formate, 0.25 g of 7E and 250 mg of progesterone) and microparticles not including progesterone were analyzed using a thermogravimetric analyzer (TGA 2050). Nitrogen was used as a purge gas. Change in weight of the microparticles was automatically recorded while increasing temperature at a rate of 10° C./min.

As seen in FIG. 23, up to 150° C., where progesterone and the drug are considered not to be decomposed, weight loss of the microparticle sample not including progesterone was 3.74%. In contrast, up to 150° C., weight loss of the microparticles including 250 mg of progesterone was only 0.75%. This result shows a tendency similar to the measurement of the residual content of isopropyl formate using GC. To conclude, when microparticles are prepared according to the method of the present invention, the used organic solvent is effectively removed from the emulsion droplets and the amount of the organic solvent remaining in the microparticles is very slight.

Example 8

Preparation of Microparticles Encapsulating Anastrazole

<8-1> Preparation of Microparticles Encapsulating Anastrazole Using Ethyl Acetate or Ethyl Formate Each of 7E, 4A and 2A polymers was dissolved in 4 mL of ethyl acetate. Then, 60 mg of anastrazole was dissolved to prepare a dispersed phase. The solution was added to 40 mL of 0.5% PVA aqueous solution and stirred. 5 mL of 10 M NaOH was added to the resultant o/w emulsion. After adding 40 mL of distilled water and stirring, microparticles were recovered by filtration. The microparticles were redispersed in 16 mL of 0.5% PVA aqueous solution. After adding distilled water to make 80 mL, the solution was stirred. After filtration, the microparticles were dried overnight in a vacuum dryer.

Similarly, microparticles encapsulating progesterone were prepared using ethyl formate instead of ethyl acetate and using 6 mL of 10 M NaOH.

As seen in FIG. 24 and FIG. 25, microspheres according to the method of the present invention were prepared well.

<8-2> Measurement of Anastrazole Encapsulation Ratio

Some of the microparticles prepared in Example <8-1> were accurately weighed and dissolved in 4 mL of tetrahydrofuran. After diluting 6 times with 50% acetonitrile, the solution was filtered using a 0.45 μm syringe filter to remove the PLGA precipitate. Some of the filtrate (20 μl) was subjected to HPLC (Shimadzu LC-20AD, Luna 5 m C18(2) column) for measurement of anastrazole concentration. Drug encapsulation ratio (%) was calculated using the equations given in Example <7-2>.

As seen in Table 6, the microparticles according to the method of the present invention showed high encapsulation ratio and good batch reproducibility, with similar encapsulation ratios between batches. When ethyl formate was used, anastrazole encapsulation ratio was slightly lower than when ethyl acetate was used.

TABLE 6

| PLGA/quantity | Organic solvent | Encapsulation ratio (%) | | |
|---|---|---|---|---|
| | | Batch 1 | Batch 2 | Batch 3 |
| 7E/0.15 g + 4A/0.1 g | Ethyl acetate | 75.3 | 73.8 | 74.7 |
| 4A/0.25 g | Ethyl acetate | 78.1 | 74.9 | 77.6 |
| 2A/0.25 g | Ethyl acetate | 78.5 | 75.2 | 73.7 |
| 7E/0.15 g + 4A 0.1 g | Ethyl formate | 60.8 | 65.1 | 65.5 |

<8-3> HPLC Chromatogram Analysis of Anastrazole

In order to indirectly estimate whether decomposition or modification products of anastrazole are produced during the preparation of microparticles using ethyl acetate/PLGA (75:25)/NaOH as in Example <8-1>, various samples were prepared (as in Example <8-1>) and their chromatograms were analyzed.

As seen in FIG. 26, when anastrazole was encapsulated in the microparticles and then recovered, the same anastrazole identical to the standard product was recovered. Therefore, it was confirmed that no decomposition or modification products of anastrazole are produced.

Example 9

Preparation of Microparticles Encapsulating Olanzapine

<9-1> Preparation of Microparticles Encapsulating Olanzapine Using Ethyl Acetate 0.15 g of 7E and 0.1 g of 4A or 2A was dissolved in 4 mL of ethyl acetate. Then, 60 mg of olanzapine was dissolved to prepare a dispersed phase. The solution was added to 40 mL of 0.5% PVA aqueous solution and stirred. After adding 5 mL of 10 M NaOH to the resultant o/w emulsion, followed by reaction for 30 minutes, 40 mL of distilled water was further added and, after stirring, microparticles were recovered by filtration. The microparticles were redispersed in 16 mL of 0.5% PVA aqueous solution. After adding distilled water to make 80 mL, the solution was stirred. After filtration, the microparticles were dried overnight in a vacuum dryer.

As seen in FIG. 27, microspheres according to the method of the present invention were prepared well.

<9-2> Measurement of Olanzapine Encapsulation Ratio

Some of the microparticles including olanzapine were accurately weighed and dissolved in 4 mL of tetrahydrofuran. After diluting 6 times with ethanol, the solution was filtered using a 0.45 μm syringe filter to remove the PLGA precipitate. Some of the filtrate (20 μl) was subjected to HPLC (Shimadzu LC-20AD, Luna 5 m C18(2) column) for measurement of olanzapine concentration. Drug encapsulation ratio (%) was calculated using the equations given in Example <7-2>.

As seen in Table 7, the microparticles prepared according to the method of the present invention showed high olanzapine encapsulation ratio and good batch reproducibility, with similar encapsulation ratios between batches. Encapsulation ratio of 7E/4A formulation was 83.5±4.4%, and that for 7E/2A was 79.8±2.7%.

TABLE 7

| PLGA/quantity | Organic solvent | Encapsulation ratio (%) | | | |
|---|---|---|---|---|---|
| | | Batch 1 | Batch 2 | Batch 3 | Batch 4 |
| 7E/0.15 g + 4A/0.1 g | Ethyl acetate | 84.3 | 82.8 | 78.1 | 88.8 |
| 7E/0.15 g + 2A/0.1 g | Ethyl acetate | 81.0 | 81.1 | 75.8 | 81.3 |

Example 10

Preparation of Microparticles Encapsulating Risperidone

<10-1> Preparation of Microparticles Encapsulating Risperidone Using Ethyl Formate 0.25 g of 4A was dissolved in 4 mL of ethyl formate. Then, 60 mg of risperidone was dissolved to prepare a dispersed phase. The solution was added to 40 mL of 0.5% PVA aqueous solution and stirred. After adding 5 mL of 8 M NaOH to the resultant o/w emulsion, followed by reaction for 30 minutes, 40 mL of distilled water was further added and, after stirring, microparticles were recovered by filtration. The microparticles were redispersed in 16 mL of 0.5% PVA aqueous solution. After adding distilled water to make 80 mL, the solution was stirred. After filtration, the microparticles were dried overnight in a vacuum dryer.

As seen in FIG. 28, microspheres according to the method of the present invention were prepared well.

<10-2> Measurement of Risperidone Encapsulation Ratio

Some of the microparticles including risperidone were accurately weighed and dissolved in 4 mL of tetrahydrofuran. After diluting 6 times with ethanol, the solution was filtered to remove the PLGA precipitate. Some of the filtrate (20 μl) was subjected to HPLC (Shimadzu LC-20AD) for measurement of risperidone concentration. Drug encapsulation ratio (%) was calculated using the equations given in Example <7-2>.

As seen in Table 8, the microparticles prepared according to the method of the present invention showed high risperidone encapsulation ratio and good batch reproducibility, with similar encapsulation ratios between batches. Average encapsulation ratio of 3 batches was 75.0±1.4%.

TABLE 8

| PLGA/quantity | Organic solvent | Encapsulation ratio (%) | | |
|---|---|---|---|---|
| | | Batch 1 | Batch 2 | Batch 3 |
| 4A/0.25 g | Ethyl formate | 75.2 | 73.6 | 76.3 |

Example 11

Preparation of Microparticles Encapsulating Aripiprazole

<11-1> Preparation of Microparticles Encapsulating Aripiprazole Using Ethyl Formate 0.25 g of 4A was dissolved in 4 mL of ethyl formate. Then, 60 mg of aripiprazole was dissolved to prepare a dispersed phase. The solution was added to 40 mL of 0.5% PVA aqueous solution and stirred. After adding 5 mL of 8 M NaOH to the resultant o/w emulsion, followed by reaction for 30 minutes, 40 mL of distilled water was further added and, after stirring, microparticles were recovered by filtration. The microparticles were redispersed in 16 mL of 0.5% PVA aqueous solution. After adding distilled water to make 80 mL, the solution was stirred. After filtration, the microparticles were dried overnight in a vacuum dryer.

As seen in FIG. 29, microspheres according to the method of the present invention were prepared well.

<11-2> Measurement of Aripiprazole Encapsulation Ratio

Some of the microparticles including aripiprazole were accurately weighed and dissolved in 4 mL of tetrahydrofuran. After diluting 6 times with ethanol, the solution was filtered to remove the PLGA precipitate. Some of the filtrate (20 μl) was subjected to HPLC (Shimadzu LC-20AD) for measurement of aripiprazole concentration. Drug encapsulation ratio (%) was calculated using the equations given in Example <7-2>.

As seen in Table 9, the microparticles prepared according to the method of the present invention showed high aripiprazole encapsulation ratio and good batch reproducibility, with similar encapsulation ratios between batches. Average encapsulation ratio of 3 batches was 72.3±2.0%.

TABLE 9

| PLGA/quantity | Organic solvent | Encapsulation ratio (%) | | |
|---|---|---|---|---|
| | | Batch 1 | Batch 2 | Batch 3 |
| 4A/0.25 g | Ethyl formate | 72.2 | 74.3 | 70.3 |

Example 12

Preparation of Microparticles Encapsulating Docetaxel, Piroxicam, Rivastigmine, Tolterodine <12-1> Preparation of Microparticles Encapsulating Docetaxel, Piroxicam, Rivastigmine or Tolterodine 50 mg of docetaxel was dissolved in 4 mL of ethyl acetate, 50 mg of piroxicam was dissolved in 4 mL of ethyl formate, 40 μl of rivastigmine was dissolved in 4 mL of ethyl formate, and 40 mg of tolterodine was dissolved in 4 mL of ethyl formate. Then, 0.25 g of 7E was dissolved to prepare a dispersed phase. The solution was added to 40 mL of 0.5% PVA aqueous solution and stirred. After adding 5 mL of 7 M NaOH to the resultant o/w emulsion, followed by reaction for 30 minutes, 40 mL of distilled water was further added and, after stirring, microparticles were recovered by filtration. The microparticles were redispersed in 16 mL of 0.5% PVA aqueous solution. After adding distilled water to make 80 mL, the solution was stirred. After filtration, the microparticles were dried overnight in a vacuum dryer.

<12-2> Measurement of Encapsulation Ratio of Docetaxel, Piroxicam, Rivastigmine or Tolterodine Some of the microparticles including each of docetaxel, piroxicam, rivastigmine or tolterodine were accurately weighed and dissolved in 4 mL of tetrahydrofuran. After diluting 6 times with ethanol, the solution was filtered to remove the PLGA precipitate. Some of the filtrate (20 μl) was subjected to HPLC (Shimadzu LC-20AD) for measurement of docetaxel, piroxicam, rivastigmine or tolterodine concentration, respectively. Drug encapsulation ratio (%) was calculated using the equations given in Example <7-2>.

As seen in Table 10, the microparticles prepared according to the method of the present invention showed high drug encapsulation ratio.

TABLE 10

| Drug | Organic solvent | Encapsulation ratio (%) | | |
|---|---|---|---|---|
| | | Batch 1 | Batch 2 | Batch 3 |
| docetaxel | Ethyl acetate | 83.2 | 80.2 | 84.2 |
| piroxicam | Ethyl formate | 76.2 | 81.2 | 79.2 |
| rivastigmine | Ethyl acetate | 74.2 | 79.2 | 78.1 |
| tolterodine | Ethyl formate | 70.3 | 77.3 | 73.2 |

As described above, the present invention provides a novel method for preparing a polymeric microsphere comprising the step of removing a water-insoluble organic solvent using a base or an acid, a polymeric microsphere prepared by the method, and a composition for drug delivery comprising the polymeric microsphere. According to the present invention, a drug-containing polymer microsphere may be prepared quickly and simply without the solvent evaporation or solvent extraction process, thereby reducing water consumption and minimizing wastewater generation. Therefore, the present invention can be effectively used in pharmaceutical and/or medical industry.

The invention claimed is:

1. A method for preparing a polymeric microsphere, including:
   (a) preparing an oil-in-water (O/W), oil-in-oil (O/O) or water-in-oil-in-water (W/O/W) emulsion including a polymer compound, a drug, a water-insoluble organic solvent and a dispersion solvent and
   (b) adding to the emulsion prepared in (a) a base solution or an acid solution to remove the water-insoluble organic solvent from the emulsion,
   wherein the base or the acid solution converts, through hydrolysis, the water-insoluble organic solvent in an aqueous phase of the emulsion into a water-soluble solvent;
   wherein the water-insoluble organic solvent in an oil phase of the emulsion diffuses into the aqueous phase, subsequently followed by conversion through hydrolysis into a water-soluble solvents, thereby hardening of an emulsion droplet into the polymeric microsphere;
   wherein the polymer compound is one selected from the group consisting of polyactic acid, polylactide, polylactic-co-glycolic acid, polylactide-co-glycolide (PLGA), polyphosphazine, polyiminocarbonate, polyphosphoester, polyanhydride, polyorthoester, a copolymer of lactic acid and caprolactone, polycaprolactone, polyhydroxyvalerate, polyhydroxybutyrate, polyamino acid, a copolymer of lactic acid and amino acid, and a mixture thereof; and
   wherein the water-insoluble organic solvent is one selected from the group consisting of methyl acetate, ethyl acetate, propyl acetate, isopropyl acetate, butyl acetate, methyl formate, ethyl formate, isopropyl formate, propyl formate, butyl formate, methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, maleic anhydride, acetic anhydride, propionic anhydride, phosphoric anhydride, acetamide, propionamide, butylamide and carboxylamide.

2. The method of claim 1, wherein the drug is one or more selected from the group consisting of progesterone, haloperidol, thiothixene, olanzapine, clozapine, bromperidol, pimozide, risperidone, ziprasidone, diazepma, ethyl loflazepate, alprazolam, nemonapride, fluoxetine, sertraline, venlafaxine, donepezil, tacrine, galantamine, rivastigmine, selegiline, ropinirole, pergolide, trihexyphenidyl, bromocriptine, benztropine, colchicine, nordazepam, etizolam, bromazepam, clotiazepam, mexazolum, buspirone, goserelin acetate, somatotropin, leuprolide acetate, octreotide, cetrorelix, sandostatin acetate, gonadotropin, fluconazole, itraconazole, mizoribine, cyclosporin, tacrolimus, naloxone, naltrexone, cladribine, chlorambucil, tretinoin, carmusitne, anagrelide, doxorubicin, anastrozole, idarubicin, cisplatin, dactinomycin, docetaxel, paclitaxel, raltitrexed, epirubicin, letrozole, mefloquine, primaquine, oxybutynin, tolterodine, allylestrenol, lovostatin, simvastatin, provastatin, atrovastatin, alendronate, salcatonin, raloxifene, oxadrolone, conjugated estrogen, estradiol, estradiol valerate, estradiol benzoate, ethinyl estradiol, etonogestrel, levonorgestrel, tibolone, norethisterone and piroxicam.

3. The method of claim 1, wherein the dispersion solvent is an aqueous dispersion solvent which is selected from the group consisting of polyvinyl alcohol aqueous solution, aqueous solution of polysorbates, and co-solvent thereof, or non-aqueous dispersion solvent which is selected from the group consisting of vegetable oil, toluene, xylene and silicon oil, wherein the non-aqueous dispersion solvent contains emulsifier which is glycerin esters of fatty acids or lecithin.

4. The method of claim 1, wherein the base is selected from the group consisting of NaOH, LiOH, KOH, $Cu(OH)_2$ and $Fe(OH)_3$.

5. The method of claim 1, wherein the acid is HCl, $HNO_3$, $H_2SO_4$, $CH_3COOH$, $H_3BO_3$, or $H_2CO_3$.

6. A polymer microsphere prepared by the method of claim 1.

7. A composition for drug delivery comprising the polymer microsphere of claim 6 as an effective ingredient.

* * * * *